United States Patent
An et al.

(10) Patent No.: US 8,008,026 B2
(45) Date of Patent: *Aug. 30, 2011

(54) METHODS FOR DIFFERENTIALLY DETECTING A MULTIMERIC FORM FROM A MONOMERIC FORM OF A MULTIMER-FORMING POLYPEPTIDE THROUGH THREE-DIMENSIONAL INTERACTIONS

(75) Inventors: Seong Soo Alexander An, Ithaca, NY (US); Kun Taek Lim, Seoul (KR); Hyun Jung Oh, Seoul (KR)

(73) Assignee: Peoplebio, Inc., Seoul (KR)

( * ) Notice: Subject to any disclaimer, the term of this patent is extended or adjusted under 35 U.S.C. 154(b) by 201 days.

This patent is subject to a terminal disclaimer.

(21) Appl. No.: 12/297,212

(22) PCT Filed: Apr. 20, 2007

(86) PCT No.: PCT/KR2007/001947
§ 371 (c)(1),
(2), (4) Date: Oct. 21, 2008

(87) PCT Pub. No.: WO2007/123345
PCT Pub. Date: Nov. 1, 2007

(65) Prior Publication Data
US 2010/0021943 A1    Jan. 28, 2010

(30) Foreign Application Priority Data

Apr. 21, 2006 (KR) .................. 10-2006-0036434
Jun. 22, 2006 (KR) .................. 10-2006-0056429

(51) Int. Cl.
*G01N 33/53* (2006.01)
(52) U.S. Cl. ........ 435/7.1; 435/7.2; 435/7.91; 435/7.92; 436/518
(58) Field of Classification Search .......... None
See application file for complete search history.

(56) References Cited

U.S. PATENT DOCUMENTS

| 4,208,479 | A  | * | 6/1980 | Zuk et al. ............... 435/7.9 |
| 6,765,088 | B1 |   | 7/2004 | Korth et al. |
| 6,846,640 | B2 |   | 1/2005 | Peach et al. |
| 6,913,896 | B1 | * | 7/2005 | Raven et al. .......... 435/7.92 |
| 2006/0057671 | A1 |   | 3/2006 | Orser et al. |
| 2007/0077603 | A1 | * | 4/2007 | Heeb et al. ............ 435/7.5 |

FOREIGN PATENT DOCUMENTS

| WO | 02/097444 A2  | 12/2002 |
| WO | 2006/088281 A1 | 10/2008 |

OTHER PUBLICATIONS

Serbec et al. J Biol. Chem. 2004 vol. 279, p. 3694-3698.*
International Search Report (ISR) dated Aug. 1, 2007, for International Patent Application PCT/KR2007/001947.
Jiri Safar, et al., "Eight prion strains have PrPSc molecules with different conformations", Nature Medicine, Oct. 1998, pp. 1157-1165, vol. 4, No. 10.

* cited by examiner

*Primary Examiner* — Jacob Cheu
(74) *Attorney, Agent, or Firm* — The Nath Law Group; Joshua B. Goldberg; Mihsuhn Koh

(57) ABSTRACT

The present invention relates to a method for differentially detecting a multimeric form from a monomeric form of a multimer-forming polypeptide in a biosample, which comprises the steps of: (a) preparing a carrier-capturing antibody conjugate by binding a capturing antibody to the surface of a solid phase carrier in a three dimensional manner, wherein the capturing antibody is capable of recognizing an epitope on the multimer-forming polypeptide; (b) preparing a detection antibody, wherein an epitope recognized by the detection antibody is present at a position in the multimer-forming polypeptide to cause a steric hindrance by the capturing antibody bound to its epitope to prevent the binding of the detection antibody to the multimer-forming polypeptide; (c) contacting simultaneously the carrier-capturing antibody conjugate and the detection antibody to the biosample; and (d) detecting the formation of a carrier-capturing antibody-multimeric form-detection antibody complex.

22 Claims, 23 Drawing Sheets

Plasma conc.:
3E7-Mag beads/T2HRP (Tricine)

T2/MA1, MDS-3D-Dual bead system

METHODS FOR DIFFERENTIALLY DETECTING A MULTIMERIC FORM FROM A MONOMERIC FORM OF A MULTIMER-FORMING POLYPEPTIDE THROUGH THREE-DIMENSIONAL INTERACTIONS

BACKGROUND OF THE INVENTION

1. Field of the Invention

The present invention relates to methods for differentially detecting a multimeric form from a monomeric form of a multimer-forming polypeptide through three-dimensional interactions and immunoassay kits therefor.

2. Description of the Related Art

A multimerization of polypeptides constituting proteins has been generally known to be required for the function of proteins. However, the multimeric forms often cause diseases or disorders in some proteins. In particular, a protein exists as a monomer in normal conditions and is converted to a multimer (or aggregate form) in abnormal conditions {e.g., by the conversion to a misfolding form).

It has been well established that proteins that are misfolded and ultimately aggregated (or accumulated), i.e., that are not in their functionally relevant conformation are devoid of normal biological activity. The failure to fold correctly, or to remain correctly folded, gives rise to many different types of biological malfunctions and hence, to many different forms of diseases (Massimo Stefani, et al., *J. Mol. Med.* 81:678-699 (2003); and Radford S E, et al., *Cell.* 97:291-298 (1999)). Many diseases ultimately result from the presence in a living system of protein molecules with structures that are incorrect, i.e., that differ from those in normally functioning organisms.

For instance, the diseases or disorders associated with abnormal aggregation or misfolding of proteins include Alzheimer's disease, Creutzfeldt-Jakob disease, Spongiform encephalopathies, Parkinson's disease, Huntington's disease, Amyotrophic lateral sclerosis, Serpin deficiency, emphysema, cirrhosis, Type II Diabetes, primary systemic amyloidosis, secondary systemic amyloidosis Fronto-temporal dementias, senile systemic amyloidosis, familial amyloid polyneuropathy, hereditary cerebral amyloid angiopathy and haemodialysis-related amyloidosis.

Early diagnosis of the aggregation-associated diseases has been intensively studied. However, there has not been suggested any process and approach to differentially detect multimeric (aggregating) forms from their monomeric (normal) forms.

Sporadic, variant, iatrogenic, and familial Creutzfeldt-Jakob diseases, kuru, Familial Fatal insomnia, and Gerstmann-Straussler-Scheinker syndrome in humans, scrapie in sheep and goats, feline spongiform encephalopathy in cat, mink spongiform encephalopathy, Chronic Wasting disease in deer, elk, and moose, and bovine spongiform encephalopathy in cattle are the fatal neurodegenerative diseases, due to transmissible spongiform encephalopathies (TSE) (Prusiner S. B. *Proc. Natl. Acad. Sci. USA* 95:13363-13383 (1998); and Hope J. *Curr. Opin. Genet Dev.* 10, 568-57 (2000)). Abnormal isoform or the scrapie form of prion protein ($PrP^{Sc}$) has been strongly suggested to the main culprit of TSE (Caughey B. *Trends Biochem. Sci.* 26:235-42 (2001)).

The normal form of the prion protein ($PrP^c$), contains both an α-helical and a flexibly disordered portion and exists as a monomeric form (Zahn, R., et al., *Proc. Natl. Acad. Sci. USA* 97:145-150 (2000)), where the scrapie form ($PrP^{Sc}$) has highly β-sheet conformation and exists as a multimeric (aggregating) or at least dimer forms (Caughey, B., et al., *J. Biol. Chem.* 273:32230-35 (1998)). The conformational change from α-helical to β-sheet conformations is the central event of the disease that seems to be responsible for its neuropathology.

While $PrP^c$ is protease sensitive ($PrP^{sen}$), $PrP^{Sc}$ is partially resistant to proteolysis ($PrP^{res}$) and prone to form high-molecular-weight aggregates (Bolton D. C. *Lancet*, 358:164-5 (2001)). This latter feature makes it difficult to analyze the conformational transition that leads to the formation of $PrP^{res}$ or to characterize it.

The method of protease K (PK) digestion has been used to discriminate the resistance of its various forms of PrP (scrapie form) by digesting the cellular form, leaving only the scrapie form to be detected in ELISA. However, the PK digestion method is being questioned. PrP conformation, concentration, tissue antibodies, digestion time and buffers could influence the PK sensitivity, which significantly reduces the reliability of the PK digestion method.

Therefore, there remains a need to develop a novel approach for differentially detecting multimeric form {e.g., $PrP^{Sc}$, scrapie form of PrP) from their monomeric forms {e.g., $PrP^c$, cellular form of PrP) with much higher reliability and convenience.

Throughout this application, various patents and publications are referenced and citations are provided in parentheses. The disclosure of these patents and publications in their entities are hereby incorporated by references into this application in order to more fully describe this invention and the state of the art to which this invention pertains.

SUMMARY OF THE INVENTION

Accordingly, it is an object of this invention to provide a method for differentially detecting a multimeric form from a monomeric form of a multimer-forming polypeptide.

It is another object of this invention to provide a kit for differentially detecting a multimeric form from a monomeric form of a multimer-forming polypeptide.

Other objects and advantages of the present invention will become apparent from the detailed description to follow and together with the appended claims and drawings.

DETAILED DESCRIPTION OF THIS INVENTION

Figure 1A:
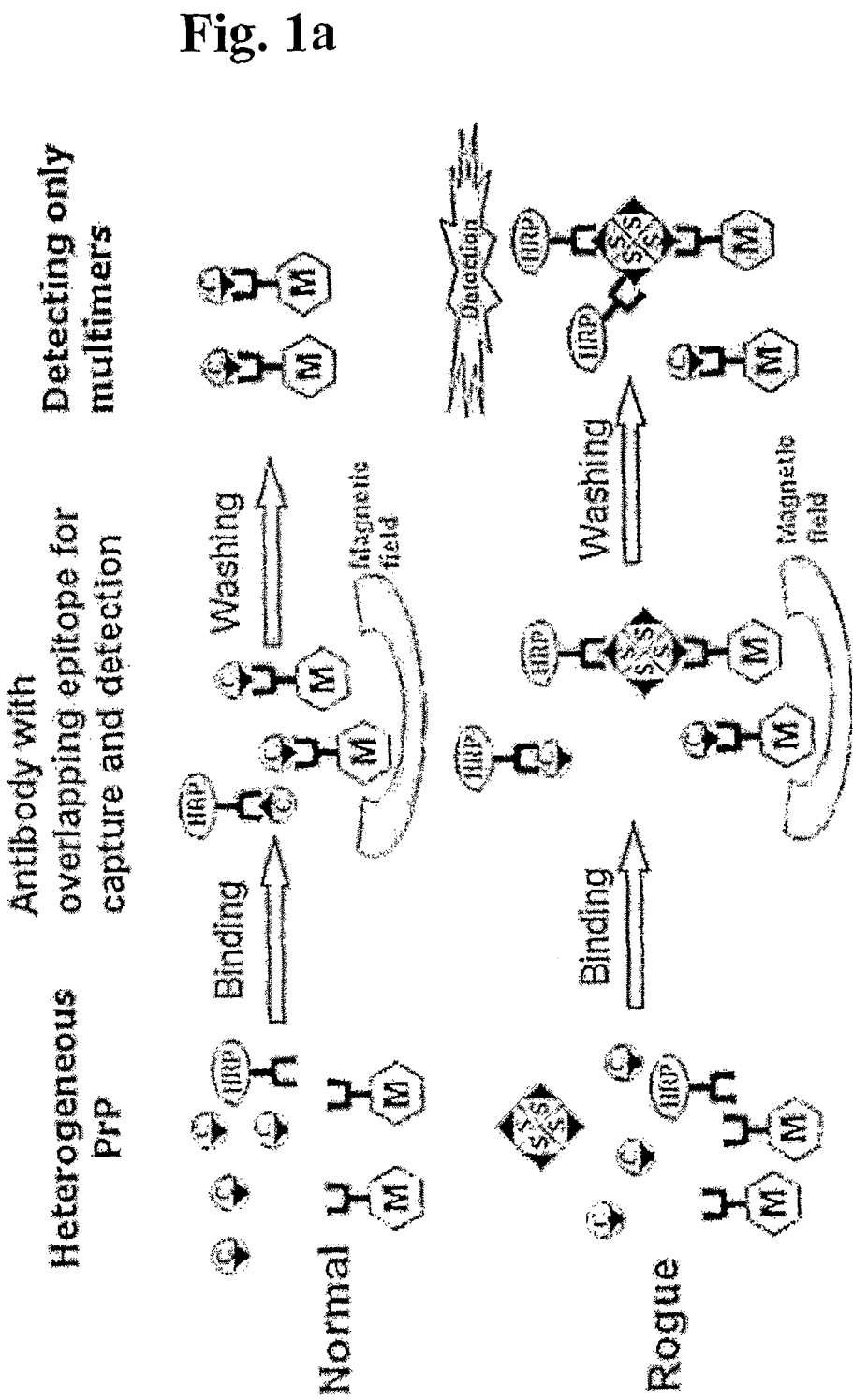
FIG. 1a schematically represents an example of the MDS-3D-Single Bead (Multimer Detection System-Three Dimensional-Single Bead) System of this invention.

In one aspect of this invention, there is provided a method for differentially detecting a multimeric form from a monomeric form of a multimer-forming polypeptide in a biosample, which comprises the steps of: (a) preparing a carrier-capturing antibody conjugate by binding a capturing antibody to the surface of a solid phase carrier in a three dimensional manner, wherein the capturing antibody is capable of recognizing an epitope on the multimer-forming polypeptide; (b) preparing a detection antibody, wherein an epitope recognized by the detection antibody is present at a position in the multimer-forming polypeptide to cause a steric hindrance by the capturing antibody bound to its epitope to prevent the binding of the detection antibody to the multimer-forming polypeptide; (c) contacting simultaneously the carrier-capturing antibody conjugate and the detection antibody to the biosample; and (d) detecting the formation of a carrier-capturing antibody-multimeric form-detection antibody complex.

In another aspect of this invention, there is provided a kit for differentially detecting a multimeric form from a monomeric form of a multimer-forming polypeptide in a biosample, which comprises: (a) a capturing antibody recognizing an epitope on the multimer-forming polypeptide and bound three-dimensionally to the surface of a solid phase carrier; and (b) a detection antibody recognizing an epitope present at a position in the multimer-forming polypeptide to cause a steric hindrance by the capturing antibody bound to its epitope to prevent the binding of the detection antibody to the multimer-forming polypeptide.

The present invention is directed to a method for differentially detecting a multimeric form from a monomeric form of a multimer-forming polypeptide in a biosample by immunoassay involving antigen-antibody reactions. Furthermore, the present invention uses two types of antibodies, a capturing antibody and a detection antibody both of which are competitive in binding to a multimer-forming polypeptide. Such competitive antibody binding occurs through steric inhibition. In particular, the capturing antibody bound to an epitope on a multimer-forming polypeptide inhibits the detection antibody from binding to its epitope on the multimer-forming polypeptide because of competition to binding sites on the multimer-forming polypeptide. One of the features of the present invention is to perform the immunoassay under three-dimensional contacting circumstances. In the present invention, the capturing and detection antibodies are ensured to have three-dimensional contacting opportunities to antigens in biosamples.

The present inventors had already proposed a prototype process for differentially detecting a multimeric form from a monomeric form of a multimer-forming polypeptide, called "Multimer Detection System (MDS)" and filed for patent application under PCT (PCT/KR2005/004001). The present invention is to improve the MDS in light of sensitivity and differentiation potential as demonstrated in Example XV. The most prominent feature of this invention is that the capturing and detection antibodies are three-dimensionally contacted to antigens in biosamples. Therefore, the process of this invention is named "MDS-3D (three-dimensional) system".

The term "multimer-forming polypeptide" used herein refers to a polypeptide capable of forming an aggregation (i.e., multimer) form, particularly, following conformational change, causing a wide variety of diseases such as Alzheimer's disease, Creutzfeldt-Jakob disease, Spongiform encephalopathies, Parkinson's disease, Huntington's disease, Amyotrophic lateral sclerosis, Serpin deficiency, emphysema, cirrhosis, Type II diabetes, primary systemic amyloidosis, secondary systemic amyloidosis Fronto-temporal dementias, senile systemic amyloidosis, familial amyloid polyneuropathy, hereditary cerebral amyloid angiopathy and haemodialysis-related amyloidosis. Therefore, the term "multimer-forming polypeptide" will be interchangeably used with the term "aggregate-forming polypeptide".

The present method uses two types of antibodies, i.e., capturing antibody and detecting antibody. As used herein, the term "capturing antibody" means an antibody capable of binding to the multimer-forming polypeptide of interest in biosamples. The term "detecting antibody" means an antibody capable of binding to the multimer-forming polypeptide captured by the capturing antibody. By "antibody" is meant an immunoglobulin protein which is capable of binding an antigen. Antibody as used herein is meant to include the entire antibody as well as any antibody fragments (e.g., F(abO2, Fab', Fab, Fv) capable of binding the epitope, antigen or antigenic fragment of interest.

In the present invention, the epitopes specifically recognized by the capturing antibody and detecting antibody are located at positions in multimer-forming polypeptides to cause steric hindrance (competitive binding) between antibodies to be bound to the epitopes. Preferably, the amino acid sequence of the epitope recognized by the capturing antibody is identical to, overlapped with or adjacent to that of the epitope recognized by the detection antibody. It would be readily understood that the capturing antibody and detection antibody to be bound to their epitopes induce steric hindrance or are competitive in binding where the amino acid sequence of the epitope recognized by the capturing antibody is identical to or overlapped with that of the epitope recognized by the detection antibody.

The term "overlapped with" used herein with referring to epitopes to capturing and detecting antibodies encompasses epitopes having completely or partially overlapped amino acid sequences. For example, the epitopes to T2 and 3E7 antibodies have amino acid sequences spanning amino acid 147-152 and 140-160, respectively, of a bovine prion sequence. Such epitopes can be described as completely overlapped epitopes. Furthermore, the epitopes to ICSM35 and 1E4 antibodies have amino acid sequences spanning amino acid 104-113 and 108-119, respectively, of a bovine prion sequence. Such epitopes can be described as partially overlapped epitopes.

As to the adjacent epitopes causing steric hindrance, one epitope (e.g., epitope recognized by the capturing antibody) in the multimer-forming polypeptide may be located at a position apart from the other epitope (e.g., epitope recognized by the detection antibody) so long as two antibodies are competitively bound to the adjacent epitopes.

Another feature of this invention is to bind capturing antibodies three-dimensionally to the surface of a solid phase carrier for preparing a carrier-capturing antibody conjugate. For instance, capturing antibodies are bound to the surface of three-dimensional beads for preparing a carrier-capturing antibody conjugate. Therefore, the present invention excludes capturing antibodies bound to the surface of plates because such binding is considered to be two-dimensional. The capturing antibodies bound three-dimensionally to carriers allows for contacting three-dimensionally to antigens in biosamples, ensuring much more opportunities to contact to antigens in biosamples.

Solid phase carriers conjugated with capturing antibodies may be any material having three-dimensional structure, preferably, materials isolatable by gravity, charge or magnetic force. Most preferably, the solid phase carrier is a magnetic bead.

According to a preferred embodiment, the detection antibody has a label generating a detectable signal or an affinity substance. The label includes, but not limited to, an enzymatic (e.g., alkaline phosphatase, peroxidase, β-galactosidase and β-glucosidase), a radioactive (e.g., $I^{125}$ and $C^{14}$), a fluorescent (e.g., fluorescein), a luminescent, a chemiluminescent and a FREET (fluorescence resonance energy transfer) label. The affinity substance includes biotin. Various labels and methods for labeling antibodies are well known in the art (Harlow and Lane, eds. *Antibodies: A Laboratory Manual* (1988) Cold Spring Harbor Laboratory Press, Cold Spring Harbor, N.Y.).

Where the radioactive label is used for detection antibodies, the antigen-antibody complex formed in the final step of this invention may be detected by measuring radioactivity from label. Where the detection antibody is labeled with enzymes catalyzing calorimetric reactions, the antigen-antibody complex formed may be detected by use of substrates for enzymes. For example, where the detection antibody is labeled with alkaline phosphatase, bromochloroindolylphosphate (BCIP), nitro blue tetrazolium (NBT), naphthol-AS-BI-phosphate and ECF (enhanced chemifluorescence) may be used as a substrate for color developing reactions; in the case of labeled with horseradish peroxidase, chloronaphtol, aminoethylcarbazol, diaminobenzidine, D-luciferin, lucigenin (bis-/V-methylacridinium nitrate), resorufin benzyl ether, luminol, Amplex Red reagent (10-acetyl-3,7-dihydroxyphenoxazine), TMB (3,3,5,5-tetramethylbenzidine) and ABTS (2,2-Azine-di[3-ethylbenzthiazoline sulfonate]) may be used as a substrate.

Where the detection antibody is labeled with affinity substance, the antigen-antibody complex formed may be detected by use of its binding partner linked to label generating a detectable signal (e.g., calorimetric reaction-catalyzing enzymes). For example, where the detection antibody is labeled with biotin, enzyme-conjugated streptavidin may be used for detecting the antigen-antibody complex.

Labels described above make it more feasible to detect qualitatively and quantitatively the multimeric antigen-antibody complex in the step (d). Where the detection antibody is linked to a label, the step (d) may be carried out by measuring a signal generated from the label.

The preferable antibody set consisting of capturing and detection antibodies comprises one antibody as a capturing antibody recognizing the epitope of amino acids 140-160 of bovine prion sequence and the other antibody as a detection antibody recognizing the epitope of amino acids 147-152 of bovine prion sequence. Another preferable antibody set comprises one antibody as a capturing antibody recognizing the epitope of amino acids 104-113 of bovine prion sequence and the other antibody as a detection antibody recognizing the epitope of amino acids 108-119 of bovine prion sequence.

The striking feature of this invention is that both the carrier-capturing antibody conjugate and detection antibody are contacted to biosamples in a simultaneous manner. If the capturing antibody is initially contacted and then the detection antibody is contacted to biosamples, carrier-capturing antibody conjugates are bound to most of epitopes in the multimeric form of a polypeptide to the capturing antibody, giving rise to the binding inhibition of the detection antibody. Therefore, where the step by step protocol is executed rather than the simultaneous protocol, the signal from the detection antibody binding becomes far poor. In contrast, where the capturing antibody and detection antibody are simultaneously contacted to biosamples, two types of antibodies are rendered to be under competition circumstances and their binding to an antigen depends on their concentration.

The term "simultaneously contacting" with reference to carrier-capturing antibodies and detection antibodies refers to: (i) contacting each of the carrier-capturing antibody and detection antibody to biosamples in a simultaneous manner; or (ii) contacting a mixture containing both the carrier-capturing antibody and detection antibody to biosamples.

According to a preferred embodiment, the capturing antibody bound to the carrier and the detection antibody in the step (c) are used at 5:1-1:5 mole ratio, more preferably 3:1-1:3 mole ratio, more still preferably 2:1-1:2 mole ratio, most preferably about 1:1 mole ratio of the capturing antibody to the detection antibody.

Where the present method is performed according to the MDS-3D Dual Bead System, the capturing antibody bound to the carrier and the detection antibody bound to the carrier in the step (c) are used at 5:1-1:5 mole ratio, more preferably 3:1-1:3 mole ratio, most preferably about 2:1 mole ratio of the capturing antibody to the detection antibody.

The present invention makes it possible to differentially detect a multimeric form from a monomeric form of any multimer-forming polypeptide. According to a preferred embodiment, the multimer-forming polypeptide includes Aβ peptide and tau protein related to Alzheimer's disease, prion related to Creutzfeldt-Jakob disease and Spongiform encephalopathies, α-synuclein related to Parkinson's disease Ig light chains related to primary systemic amyloidosis, serum amyloid A related to secondary systemic amyloidosis, tau related to Fronto-temporal dementias, transthyretin related to senile systemic amyloidosis, transthyretin related to familial amyloid polyneuropathy, cystatin C related to hereditary cerebral amyloid angiopathy, $β_2$-microglobulin related to haemodialysis-related amyloidosis, huntingtin related to Huntington's disease, superoxide dismutase related to Amyotrophic lateral sclerosis, serpin related to Serpin deficiency, emphysema, and cirrhosis, and amylin related to Type II Diabetes.

Most preferably, the multimer-forming polypeptide is the prion protein causing Creutzfeldt-Jakob disease and Spongiform encephalopathies.

The present invention is significantly useful in detecting a multimeric prion, i.e., $PrP^{Sc}$ formed by conformational change of prion proteins.

When the present method is applied to the prion protein (PrP), the monomeric form is $PrP^c$ (cellular or normal form of prion) and the multimeric form is $PrP^{Sc}$ (scrapie or infectious form of prion).

One of the features of this invention is to employ antibodies which are bound to epitopes having non-repeated sequence in an antigen molecule. Unless epitopes recognized by antibodies have a non-repeated sequence, the present invention may not effectively detect a multimeric form from a monomeric form of a multimer-forming polypeptide.

According to a preferred embodiment, the epitope specifically recognized by the capturing antibody and/or the epitope specifically recognized by the detection antibody are not repeated in the multimer-forming polypeptide.

The antibodies used in this invention could be prepared according to conventional techniques such as a fusion method (Kohler and Milstein, *European Journal of Immunology*, 6:511-519 (1976)), a recombinant DNA method (U.S. Pat. No. 4,816,56) or a phage antibody library (Clackson et al, *Nature*, 352:624-628 (1991); and Marks et al, *J. Mol. Biol.*, 222:58, 1-597 (1991)). The general procedures for antibody production are described in Harlow, E. and Lane, D., *Antibodies: A Laboratory Manual*, Cold Spring Harbor Press, New York, 1988; Zola, H., *Monoclonal Antibodies: A Manual of Techniques*, CRC Press, Inc., Boca Raton, Fla., 1984; and Coligan, *CURRENT PROTOCOLS IN IMMUNOLOGY*, Wiley/Greene, NY, 1991. The preparation of hybridoma cell lines for monoclonal antibody production is done by fusion of an immortal cell line and the antibody producing lymphocytes. This can be done by techniques well known in the art. Polyclonal antibodies may be prepared by injection of the antigen described above to suitable animal, collecting antiserum containing antibodies from the animal, and isolating specific antibodies by any of the known affinity techniques.

The present invention also encompasses the utilization of cocktails of antibodies as capturing antibodies or detection antibodies only if the cocktailed capturing or detection antibodies are reactive to epitopes identical to or overlapped with epitopes for detection or capturing antibodies, respectively. As addressed in Examples XIII and XIV, the present invention using a cocktailed capturing or detection antibody permits to differentially detect $PrP^{Sc}$ from $PrP^c$.

The term "Biosample" used herein is an organism-originated sample of material to be tested. The biosample refers to any cell, tissue, or fluid from a biological source, or any other medium that can advantageously be evaluated according to this invention, including a sample drawn from human, a sample drawn from an animal, a sample drawn from food designed for human or animal consumption. Preferably, the biosample to be tested is a body fluid sample including blood, serum, plasma, lymph, milk, urine, feces, ocular fluid, saliva, semen, brain extracts (e.g., brain homogenates), spinal cord fluid (SCF), appendix, spleen and tonsillar tissue extracts. More preferably, the biosample is a brain homogenate or plasma, most preferably, plasma.

Where a brain homogenate is used as a biosample, it is advantageous that the present method further comprises the step of pretreating the biosample with protease K (PK) or trypsin.

Where blood or plasma is used as a biosample, it is preferable that the biosample is not pretreated with proteases {e.g., PK}. The protease treatment results in significant decrease in the detection and differentiation potentials of the present method to multimeric forms, particularly, $PrP^{Sc}$. Surprisingly, the present methods permits to completely eliminate a need of protease {e.g., PK} digestion in the detection of $PrP^{Sc}$ in blood or plasma samples, as demonstrated in Example X.

Where blood or plasma is used as a biosample, it is advantageous that the present method further comprises the step of pretreating the biosample with sarkosyl or Triton series {e.g., Triton X-IOO) detergent, preferably, Triton series, most preferably Triton X-IOO. For preparation of biosamples (preferably blood, most preferably plasma), a preferable buffer includes TBST (tris-buffered saline with Tween 20) and Tricine. Preferably, the concentration of biosamples (preferably blood, most preferably plasma) in the step (c) ranges from 10 v/v % to 70 v/v %, more preferably, from 20 v/v % to 40 v/v %, most preferably from 23 v/v % to 30 v/v %.

In still another aspect of this invention, there is provided a method for differentially detecting a multimeric form from a monomeric form of a multimer-forming polypeptide in a biosample, which comprises the steps of: (a) preparing a magnetic bead-capturing antibody conjugate by binding a capturing antibody to the surface of a magnetic bead in a three dimensional manner, wherein the capturing antibody is capable of recognizing an epitope on the multimer-forming polypeptide; (b) preparing a detection antibody, wherein an epitope recognized by the detection antibody is present at a position in the multimer-forming polypeptide to cause a steric hindrance by the capturing antibody bound to its epitope to prevent the binding of the detection antibody to the multimer-forming polypeptide; (c) contacting simultaneously the magnetic bead-capturing antibody conjugate and the detection antibody to the biosample; (d) applying the resultant of step (c) to isolate a magnetic bead-capturing antibody-multimeric form-detection antibody complex; and (e) detecting the formation of the magnetic bead-capturing antibody-multimeric form-detection antibody complex.

Preferably, the method of this invention further comprises the step of washing the isolated capturing antibody-multimeric form-detection antibody complex between the step (d) and the step (e). The washing step may be carried out using various washing buffers such as PBS (phosphate-buffered saline), PBST (phosphate-buffered saline with Tween 20), PBSX (phosphate-buffered saline with Triton X-IOO), TBSX (tris-buffered saline with Triton X-IOO) and TBST (tris-buffered saline with Tween 20). Most preferably, the washing step is performed using TBST.

FIG. 1a schematically represents an example of this invention using magnetic beads as carriers. The present invention will be described in more detail with referring to FIG. 1a. The capturing antibodies on magnetic beads and the HRP-detection antibodies are simultaneously contacted to biosamples containing $PrP^c$ and $PrP^{Sc}$, HRP-conjugated detection antibodies cannot be bound to magnetic bead-capturing antibody-bound $PrP^c$ but bound only to magnetic bead-capturing antibody-bound $PrP^{Sc}$. In addition, magnetic bead-capturing antibodies cannot be also bound to HRP-conjugated detection antibody-bound $PrP^c$. The epitopes to the capturing antibody and detection antibody have a non-repeated sequence in the prion protein. The amino acid sequence of the epitope recognized by the capturing antibody is identical to, overlapped with or adjacent to that of the epitope recognized by the detection antibody. In FIG. 1a, epitopes are denoted as triangle. Since the epitope recognized by the detection antibody is occupied by the capturing antibody, the detection antibody cannot be bound to $PrP^c$ having only one epitope. However, since the multimeric prion protein, $PrP^{Sc}$ contains a plurality of certain epitope, the detection antibody can be bound to capturing antibody-bound $PrP^{Sc}$. After the antigen-antibody reaction, a magnetic field is applied to the reaction resultant to collect magnetic beads, followed by washing the collected beads. The color-, fluorescence- or luminescence-developing reactions are induced using HRP substrates and their results are measured, providing qualitative and quantitative analysis data to verify whether the $PrP^{Sc}$-antibody complex is formed.

According to a preferred embodiment of this kit, the capturing antibody bound to the carrier and the detection antibody are contained at 5:1-1:5 mole ratio, more preferably 3:1-1:3 mole ratio, more still preferably 2:1-1:2 mole ratio, most preferably about 1:1 mole ratio of the capturing antibody to the detection antibody in the form of mixture. The kit may further comprise magnetic plate, buffer, color-developing enzymes and substrates.

The MDS-3D System of this invention is classified into MDS-3D Single Bead System and MDS-3D Dual Bead System.

Figure 1B:
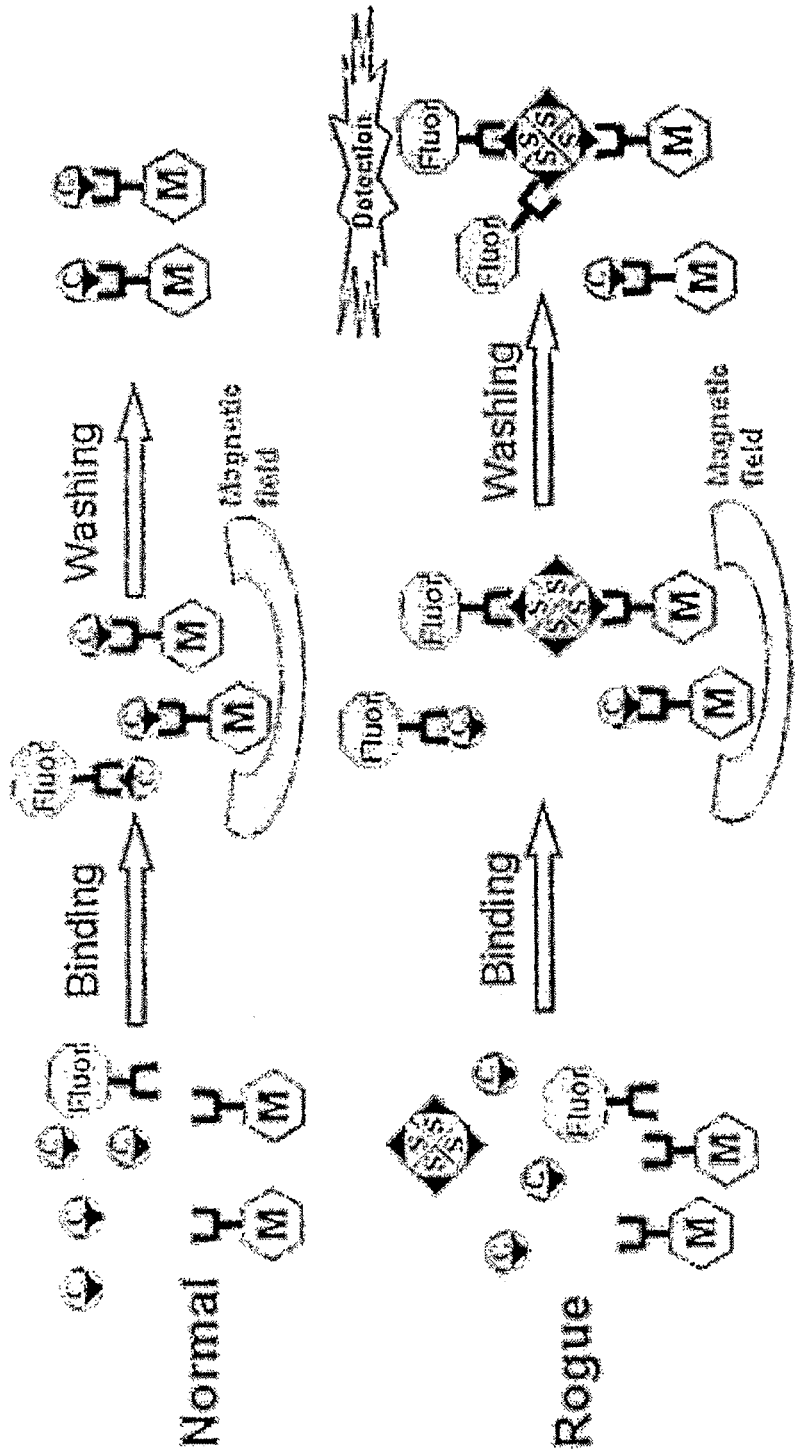
FIG. 1b schematically represents an example of the MDS-3D-Dual Bead System of this invention.
Figure 1C:
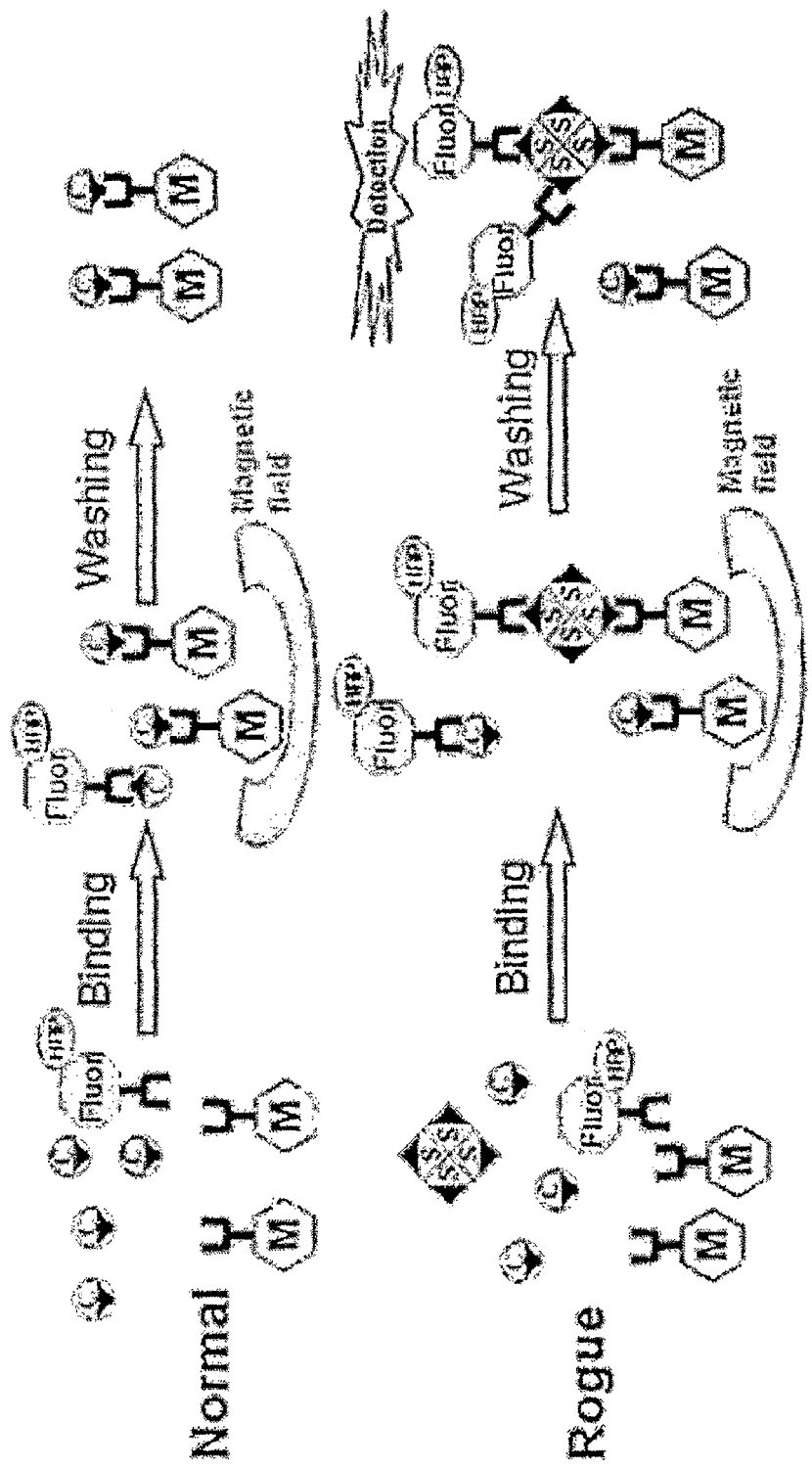
FIG. 1c schematically represents an example of the MDS-3D-Dual Bead System with double label of this invention.

The MDS-3D Single Bead System uses capturing antibody-conjugated beads (FIG. 1a) and the MDS-3D Dual Bead System uses both capturing antibody-conjugated beads and detection antibody-conjugated beads (FIGS. 1b and 1c). The MDS-3D Single Bead System is described hereinabove with reference to FIG. 1a.

In the MDS-3D Dual Bead System, the detection antibody is three-dimensionally linked to the surface of a solid phase carrier. The detection antibodies bound to carriers permit to contact to multimeric polypeptides in a three-dimensional manner.

Solid phase carriers conjugated with detection antibodies may be any material having three-dimensional structure, preferably, materials isolatable by gravity, charge or magnetic force. Most preferably, the solid phase carrier is a latex bead. The carrier may be labeled. Where the carrier has a label (e.g., the carrier is a latex beads containing fluorescent substance), a detectable signal generated from the carrier (indicative of the presence of multimeric polypeptides) may be obtained without labeling detection antibodies.

The MDS-3D Dual Bead System is further classified into "MDS-3D Dual Bead System with Single Label" (FIG. 1b) and "MDS-3D Dual Bead System with Double Label" (FIG. 1c).

In the MDS-3D Dual Bead System with Single Label, either detection antibody or carrier has a label generating a detectable signal. Both detection antibody and carrier have a label generating a detectable signal in the MDS-3D Dual Bead System with Double Label. Such double labeling strategy enables to doubly check a signal indicative of the presence of multimeric polypeptides.

The MDS-3D Dual Bead System with Single Label will be described in more detail with referring to FIG. 1b. The capturing antibodies on magnetic beads and Fluor-detection antibodies (detection antibodies linked to latex beads containing fluorescent substance) are simultaneously contacted to biosamples containing $PrP^c$ and $PrP^{Sc}$, and Fluor-detection antibodies cannot be bound to magnetic bead-capturing antibody-bound $PrP^c$ but bound only to magnetic bead-capturing antibody-bound $PrP^{Sc}$. The epitopes to the capturing antibody and detection antibody have a non-repeated sequence in the prion protein. The amino acid sequence of the epitope recognized by the capturing antibody is identical to, overlapped with or adjacent to that of the epitope recognized by the detection antibody. In FIG. 1b, epitopes are denoted as triangle. Since the epitope recognized by the detection antibody is occupied by the capturing antibody, the detection antibody cannot be bound to $PrP^c$ having only one epitope. However, since the multimeric prion protein, $PrP^{Sc}$ contains a plurality of certain epitope, the detection antibody can be bound to capturing antibody-bound $PrP^{Sc}$. After the antigen-antibody reaction, a magnetic field is applied to the reaction resultant to collect magnetic beads, followed by washing the collected beads. Measurements are carried out to analyze fluorescence intensities, verifying whether the $PrP^{Sc}$-antibody complex is formed.

The MDS-3D Dual Bead System with Double Label will be described in more detail with referring to FIG. 1c. The capturing antibodies on magnetic beads and Fluor-HRP-detection antibodies (HRP-conjugated detection antibodies linked to latex beads containing fluorescent substance) are simultaneously contacted to biosamples containing $PrP^c$ and $PrP^{Sc}$, Fluor-detection antibodies cannot be bound to magnetic bead-capturing antibody-bound $PrP^c$ but bound only to magnetic bead-capturing antibody-bound $PrP^{Sc}$. The epitopes to the capturing antibody and detection antibody have a non-repeated sequence in the prion protein. The amino acid sequence of the epitope recognized by the capturing antibody is identical to, overlapped with or adjacent to that of the epitope recognized by the detection antibody. In FIG. 1c, epitopes are denoted as triangle. Since the epitope recognized by the detection antibody is occupied by the capturing antibody, the detection antibody cannot be bound to $PrP^c$ having only one epitope. However, since the multimeric prion protein, $PrP^{Sc}$ contains a plurality of certain epitope, the detection antibody can be bound to capturing antibody-bound $PrP^{Sc}$. After the antigen-antibody reaction, a magnetic field is applied to the reaction resultant to collect magnetic beads, followed by washing the collected beads. Measurements are carried out to analyze fluorescence intensities and HRP reactions, verifying whether the $PrP^{Sc}$-antibody complex is formed.

The following specific examples are intended to be illustrative of the invention and should not be construed as limiting the scope of the invention as defined by appended claims.

EXAMPLES

Example I

Detection of Multimeric PrP in Plasma Using MDS-3D-Single Bead System

2705 µl of sheep plasma, 22.5 µl of recombinant multimeric sheep PrP (genotype ARQ, 120-fold diluted) and 3605 µl of 2.5× detergent (including 3% Triton X-IOO, 1.5% Na deoxycholate and 0.25% sarkosyl) were mixed to prepare a sample. The negative control was also prepared to contain 22.5 µl of PBS instead of the recombinant multimeric sheep PrP. Capturing antibody-conjugated magnetic beads were prepared in which 1 µg of capturing antibodies was bound to 2.5 µl of magnetic beads. The capturing antibody bound to magnetic beads is 3E7 or MA1-750 monoclonal antibodies. The epitope against the 3E7 monoclonal antibody is an amino acid sequence spanning 140-160 of $PrP^c$ (with reference to a bovine prion sequence) or 132-152 (with reference to a sheep prion sequence), which is found to be a non-repeated sequence in prion. The MA1-750 antibody recognizes specifically an epitope on $PrP^c$, Ser-Arg-Pro-Leu-Ile-His-Phe-Gly-Ser-Asp-Tyr-Glu-Asp-Arg, which is found to be a non-repeated sequence in prion.

The capturing antibody-conjugated magnetic bead and the detection antibody were incubated with the plasma sample in a simultaneous manner. Then, we determined whether the recombinant multimeric sheep PrP in plasma samples was detected by the MDS-Single Bead System of this invention. As detection antibodies, 3B8/D5-HRP or T2-HRP was used. The T2 antibody is described in Hiroko Hayashi, et al., *J. Vet. Med. Sc/.*, 66(6):515 (2004), recognizing $PrP_{147-152}$ epitope (with reference to a bovine prion sequence) or $PrP_{140-145}$ epitope (with reference to a sheep prion sequence). The epitope against the 3B8/D5 monoclonal antibody is an amino acid sequence spanning 132-152 (with reference to a sheep prion sequence) or 140-160 (with reference to a bovine prion sequence).

The capturing antibody-conjugated magnetic bead and the detection antibody were simultaneously added to the plasma sample and incubated for 1 hr at 37° C. The magnetic field was then applied to the reaction mixture to separate magnetic beads, followed by washing the beads three times with TBST. The ECL (enhanced chemiluminescence) detection was performed.

TABLE 1

| Experiment | Antibodies | Amount of Ab |
|---|---|---|
| Exp. 1 | Bead-3E7 | 7.5 µl |
|  | 3B8/D5-HRP | 1 µl |
| Exp. 2 | Bead-3E7 | 5 µl |
|  | 3B8/D5-HRP | 2 µl |
| Exp. 3 | Bead-3E7 | 2.5 µl |
|  | 3B8/D5-HRP | 3 µl |
| Exp. 4 | Bead-3E7 | 2.5 µl |
|  | T2-HRP (36 µg/ml) | 3.3 µl |
| Exp. 5 | Bead-MA1-750 | 2.5 µl |
|  | T2-HRP (36 µg/ml) | 3.3 µl |

For comparison, the capturing antibody-conjugated magnetic bead was initially incubated with the plasma sample and then incubated with detection antibodies.

The plasma sample was prepared as described hereinabove. The capturing antibody-conjugated magnetic beads were added to the plasma sample and incubated for 1 hr at 37° C. The magnetic field was then applied to the reaction mixture to separate magnetic beads, followed by washing the beads three times with TBST. Then, the separated beads were incubated with the detection antibody for 1 hr at 37° C. The magnetic field was applied to the reaction mixture to separate magnetic beads, followed by washing the beads three times with TBST. Finally, the ECL (enhanced chemiluminescence) detection was performed.

Figure 2:
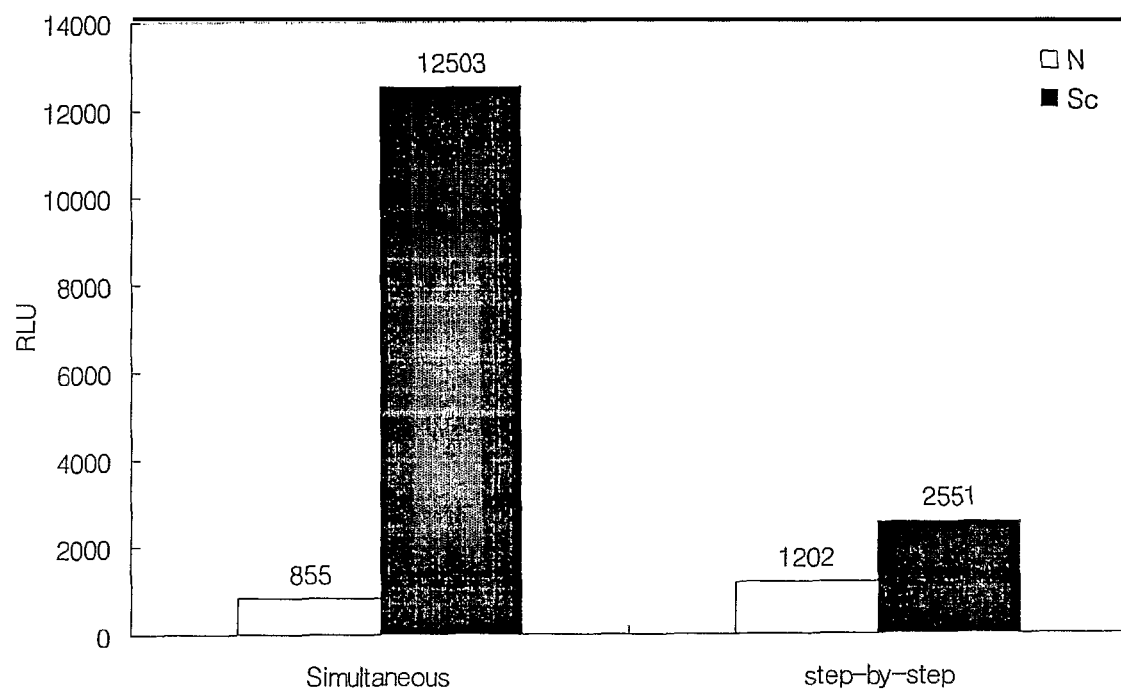
FIG. 2 shows the results of experiments for detecting multimeric prion proteins according to the present invention (simultaneous method) and conventional process (step-by-step method). "N" and "Sc" denote normal plasma and plasma containing $PrP^{Sc}$, respectively. "RLU" denotes relative light units.

As shown in FIG. 2, where the magnetic bead-capturing antibody (3E7 antibody) and the detection antibody (T2-HRP) were incubated with samples in a simultaneous manner, the detection signal to multimeric PrP was shown to be much higher than that of the step-by-step protocol, demonstrating that the simultaneous protocol dramatically increases sensitivity in the detection of multimeric prion. In addition, the ratio of signal intensity of multimeric prion to that of normal prion in the simultaneous protocol is much greater than that in the step-by-step protocol, urging us to reason that the present invention exhibits an excellent differentiation potential to multimeric prion.

Example II

Determination of Buffer Type Suitable in MDS-3D-Single Bead System

Figure 3A:
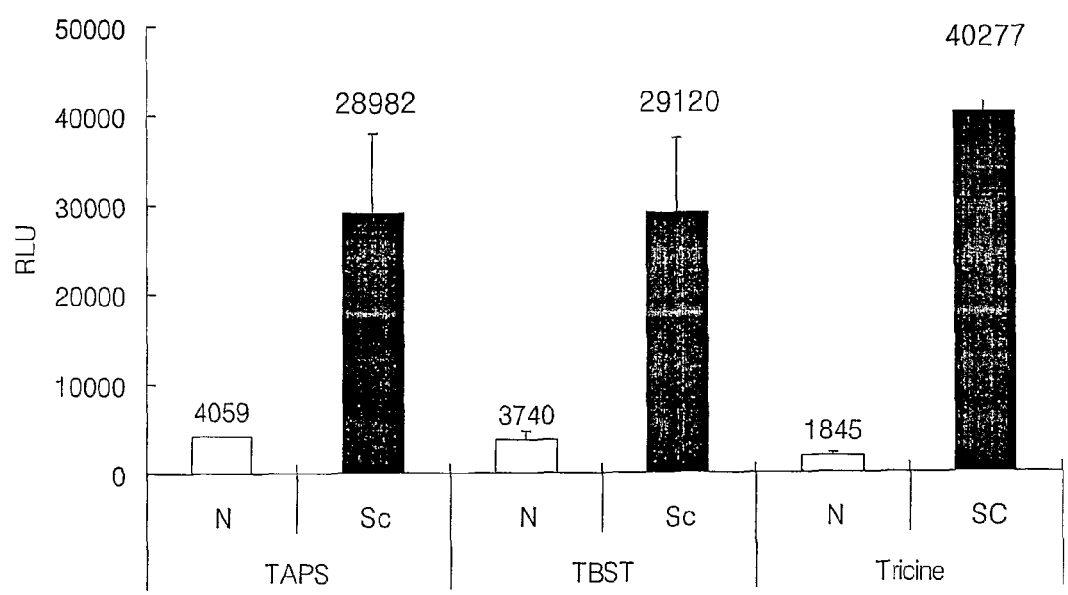
FIG. 3a represents the results of experiments for selecting a buffer type suitable in the MDS-3D-Single Bead System.
Figure 3B:
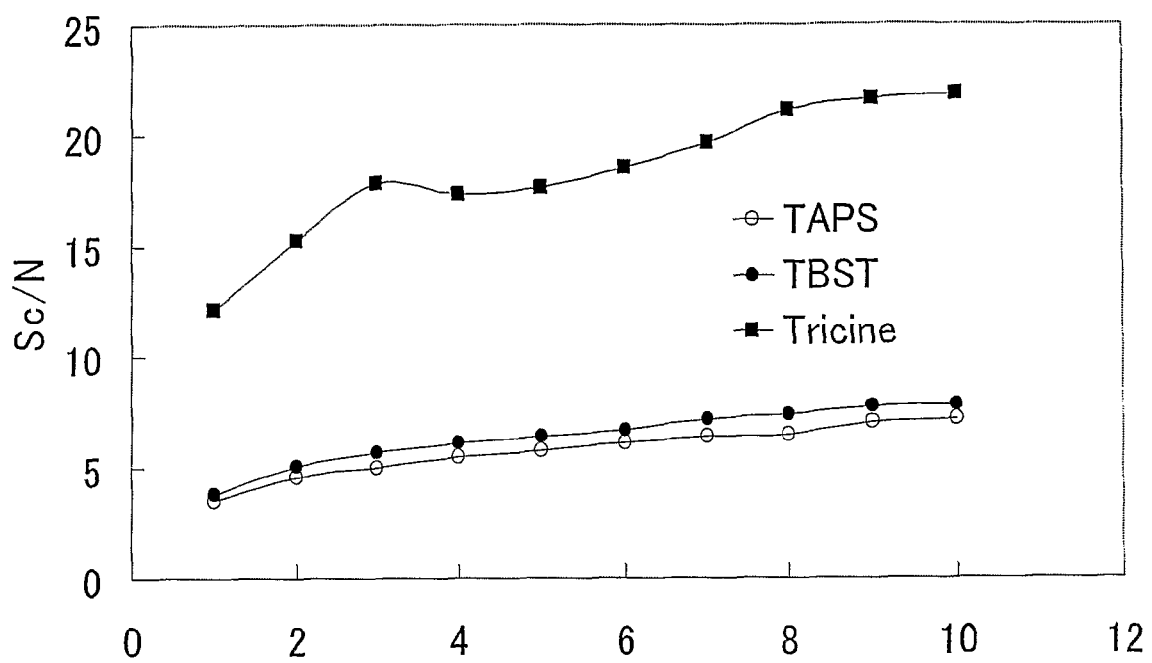
FIG. 3b shows another presentation of results of FIG. 3a represented by the ratio of the signal from $PrP^{Sc}$ plasma to the signal from normal plasma.

To determine a suitable buffer type in the MDS-3D-Single Bead System of this invention, the magnetic-bound capturing antibody, 3E7-bead and detection antibody, T2-HRP were used at a weight ratio of 1 to 1 (0.8 µg:0.8 µg, substantially correspond to a mole ratio of 1 to 1) for performing the MDS-3D-Single Bead System. Plasma samples were prepared as follows: 120 µl of 10% Triton X-100 in d-$H_2O$, 580 µl of buffer (TAPS, TBST or Tricine, pH 8.0) and 300 µl of sheep plasma showing clinical signs to have $PrP^{sc}$ were mixed to give 1 ml of the total volume of plasma sample containing 1.2% Triton X-100 and 30% plasma. 2 µl (0.8 µg) of 3E7-conjugated magnetic bead as capturing antibodies and 200 µl (0.8 µg) of T2-HRP (4 µg/ml in TBST) as detection antibodies were mixed to prepare a mixed antibody. 200 µl of the mixed antibody were added to 1 ml of the plasma sample and incubated for 1 hr at 37° C. The magnetic field was then applied to the reaction mixture to separate magnetic beads, followed by washing the beads three times with TBST. The ECL detection was performed (FIGS. 3a and 3b). In FIGS. 3a and 3b, "N" and "Sc" denote normal plasma and plasma containing $PrP^{\Xi c}$, respectively. As shown in FIGS. 3a and 3b, Tricine buffer shows the highest signal to plasma containing $PrP^{\Xi c}$ and lowest signal to normal plasma.

Example III

Detection of Multimeric PrP in Plasma Using MDS-3D-Dual Bead System

Figure 4:
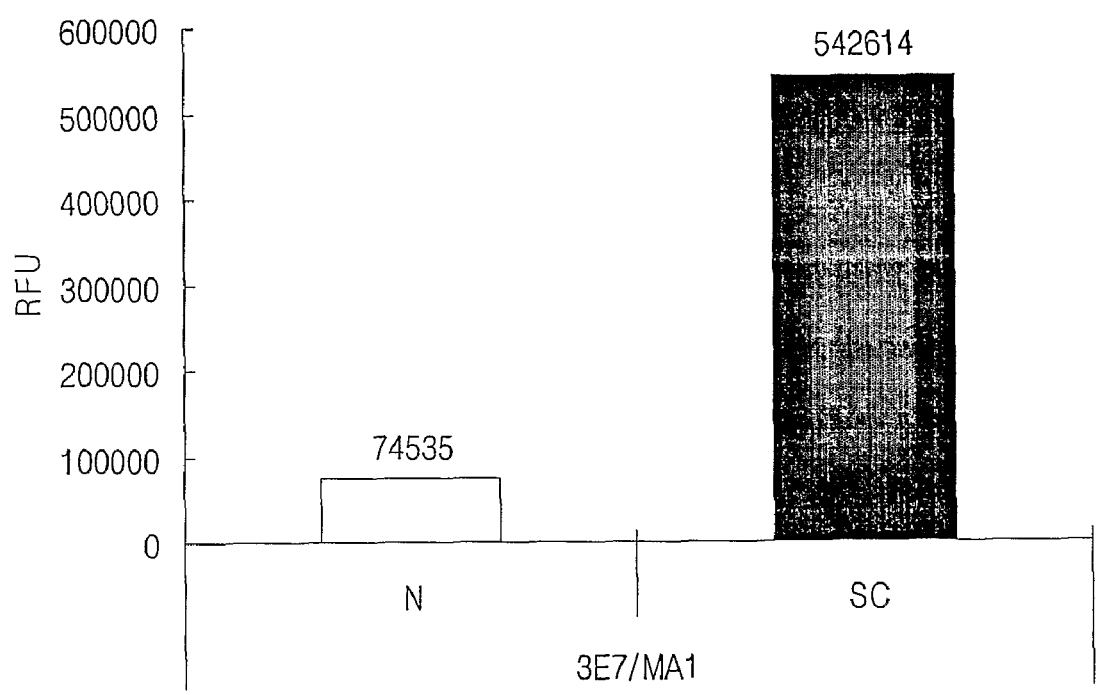
FIG. 4 shows the results of experiments for detecting multimeric prion proteins in plasma according to the MDS-3D-Dual Bead System using 3E7 and MAI 750 antibodies. "RFU" denotes relative fluorescence units.

120 µl of 10% Triton X-100, 730 µl of TBST buffer (pH 8.0) and 150 µl of sheep plasma were mixed to give 1 ml of plasma sample containing 1.2% Triton X-100 and 15% plasma. 4 µl of 3E7-conjugated magnetic bead as capturing antibodies, 2 µl of MAI 750-conjugated fluorescence latex bead as detection antibodies and 200 µl of TBST buffer were mixed to prepare a mixed antibody (3E7-bead:MAI 750-fluorescence bead, 2:1). 200 µl of the mixed antibody were added to 1 ml of the plasma sample and incubated for 1 hr at 37° C. The magnetic field was then applied to the reaction mixture to separate magnetic beads, followed by washing the beads three times with TBST. Finally, the fluorescent signal was detected. As represented in FIG. 4, the MDS-3D-Dual Bead System permits to detect differentially PrP$^{Sc}$ in plasma.

Example IV

Determination of Buffer Type Suitable in MDS-3D-Dual Bead System

Figure 5:
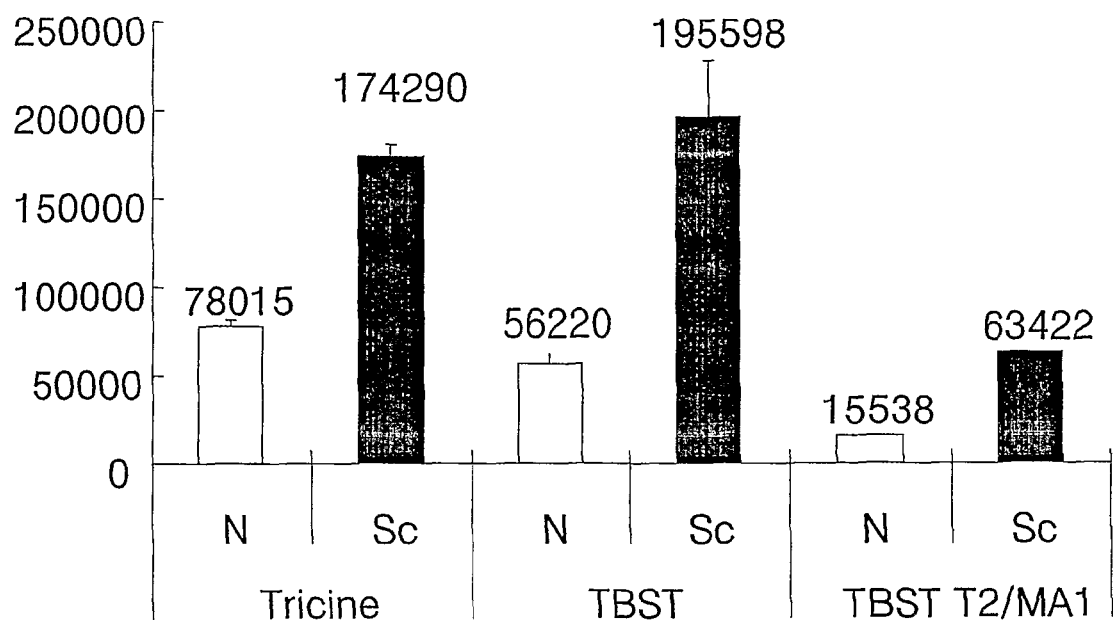
FIG. 5 represents the results of experiments for selecting a buffer type suitable in the MDS-3D-Dual Bead System.

4 µl of 3E7-conjugated magnetic bead as capturing antibodies and 1 µl of MAI 750-conjugated fluorescence latex bead as detection antibodies were mixed to prepare a mixed antibody (3E7-bead:MAI 750-fluorescence bead, 4:1). 120 µl of 10% Triton X-100, 730 µl of buffer (TBST or Tricine, pH 8.0) and 150 µl of sheep plasma were mixed to obtain a plasma sample. The other procedures are the same as Example III. As shown in FIG. 5, TBST was shown to be higher signal and differentiation potential than Tricine buffer in detection of PrP$^{Sc}$ in plasma sample using the MDS-3D-Dual Bead System.

Furthermore, the MDS-3D-Dual Bead System was made using T2 and MAI antibody as capturing and detection antibodies, respectively, and then the above-described procedures were carried out. As represented in FIG. 5, the MDS-3D-Dual Bead System using another antibody combination also allows for the detection of PrP$^{Sc}$ in plasma.

Example V

Determination of Plasma Concentration Suitable in MDS-3D-Dual Bead System

2 µl of 3E7-conjugated magnetic bead as capturing antibodies and 1 µl of MAI 750-conjugated fluorescence latex bead as detection antibodies were mixed to prepare a mixed antibody (3E7-bead:MAI 750-fluorescence bead, 2:1). Plasma samples in concentrations of 30%, 15% and 7.5% were prepared. Tricine (pH 8.0) buffer was used. The other procedures are the same as Example III.

Figure 6:
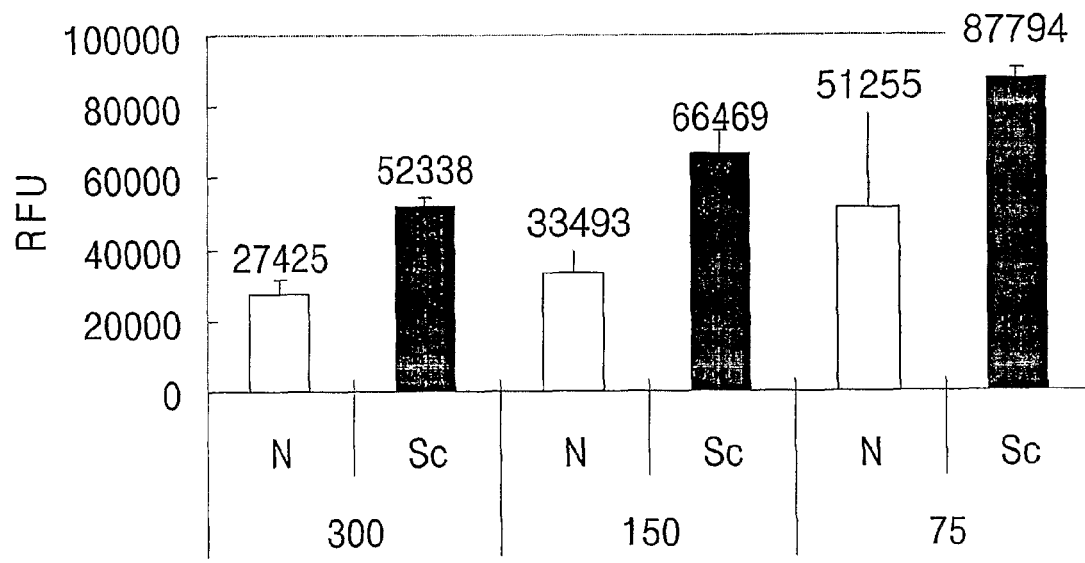
FIG. 6 represents the results of experiments for selecting concentrations of plasma suitable in the MDS-3D-Dual Bead System.

As represented in FIG. 6, the MDS-3D-Dual Bead System of this invention permits to detect differentially PrP$^{Sc}$ in all plasma samples in concentrations of 30%, 15% and 7.5%. While the ratio of Sc/N decreases upon decreasing the concentration of plasma, the intensity of signals increases upon decreasing the concentration of plasma. Accordingly, it could be appreciated that the concentration of plasma suitable in the MDS-3D-Dual Bead System is around 15%.

Example VI

Determination of Plasma Concentration Suitable in MDS-3D-Single Bead System

To determine a suitable plasma concentration in the MDS-3D-Single Bead System, the magnetic-bound capturing antibody, 3E7-bead and detection antibody, T2-HRP were used at a ratio of 1 to 1 (0.8 µg:0.8 µg) for performing the MDS-3D-Single Bead System. Plasma samples in concentrations of 30%, 15% and 7.5% were prepared. Tricine (pH 8.0) buffer was used. The other procedures are the same as Example II.

Figure 7:
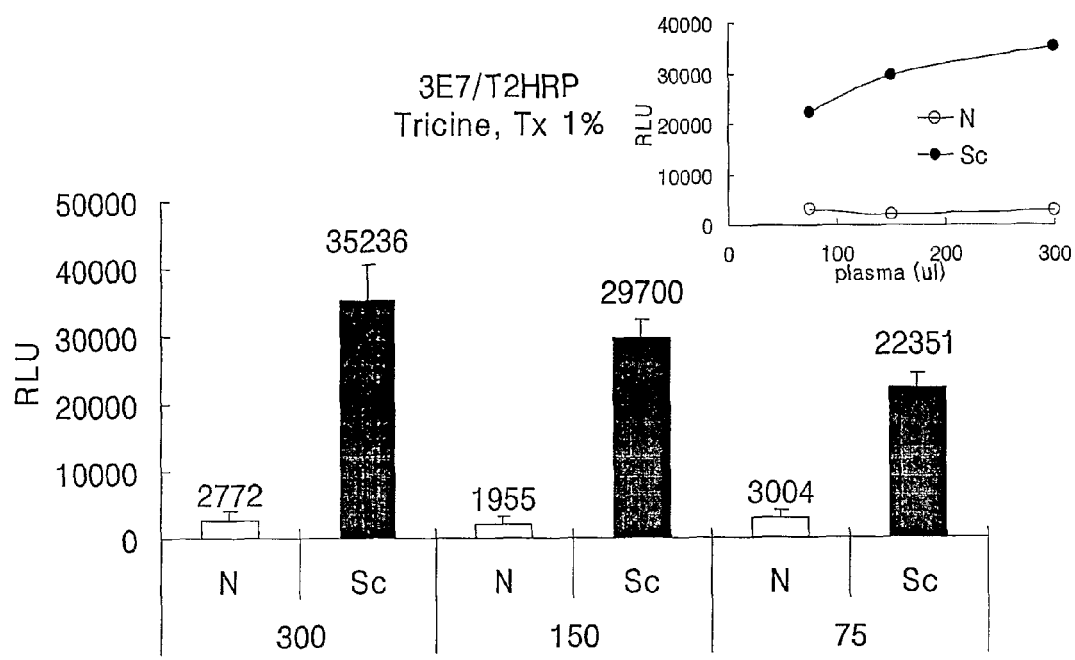
FIG. 7 represents the results of experiments for selecting concentrations of plasma suitable in the MDS-3D-Single Bead System.

As represented in FIG. 7, the MDS-3D-Single Bead System of this invention permits to detect differentially PrP$^{Sc}$ in all plasma samples in concentrations of 30%, 15% and 7.5%. The ratio of Sc/N, and the signal intensities to both normal plasma and PrP$^{Sc}$ plasma decreases upon decreasing the concentration of plasma. Accordingly, it could be understood that the concentration of plasma suitable in the MDS-3D-Single Bead System is around 30%.

Figure 11:
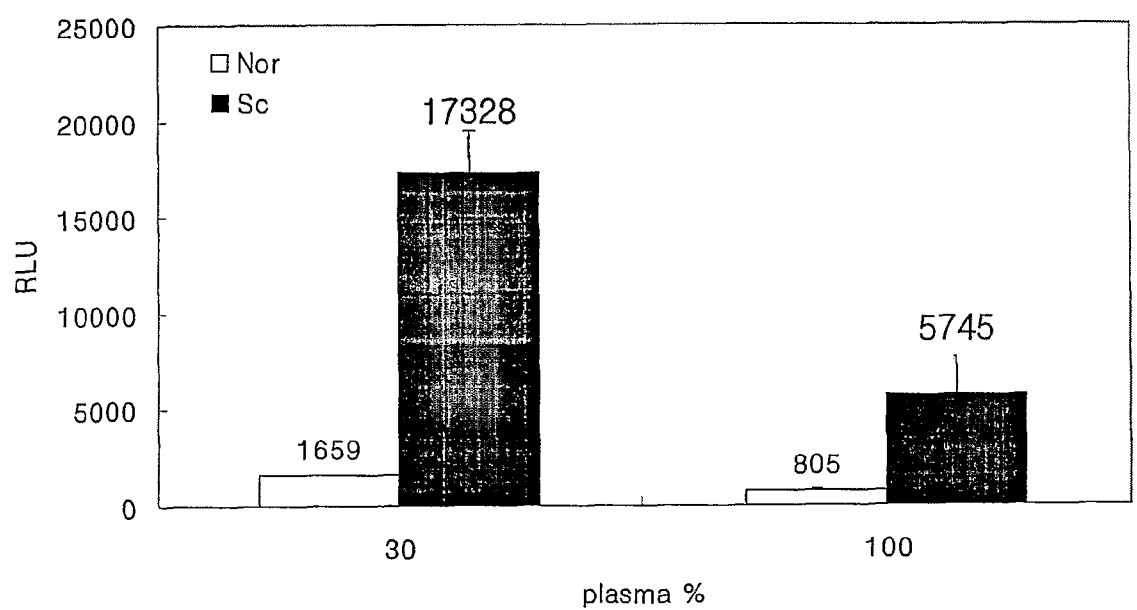
FIG. 11 represents the analysis results for detecting multimeric prion proteins in plasma with concentrations of 30% and 100% according to the MDS-3D-Single Bead System.

Furthermore, the 3E7-bead antibody and the T2-HRP antibody were used at a ratio of 1 to 2 and plasma samples in concentrations of 30% and 100% were prepared using Tricine (pH 8.0) buffer. The other procedures are the same as Example II. As shown in FIG. 11, the 100% plasma concentration was observed to produce much lower signal intensities and differentiation than 30% plasma concentration.

Figure 12:
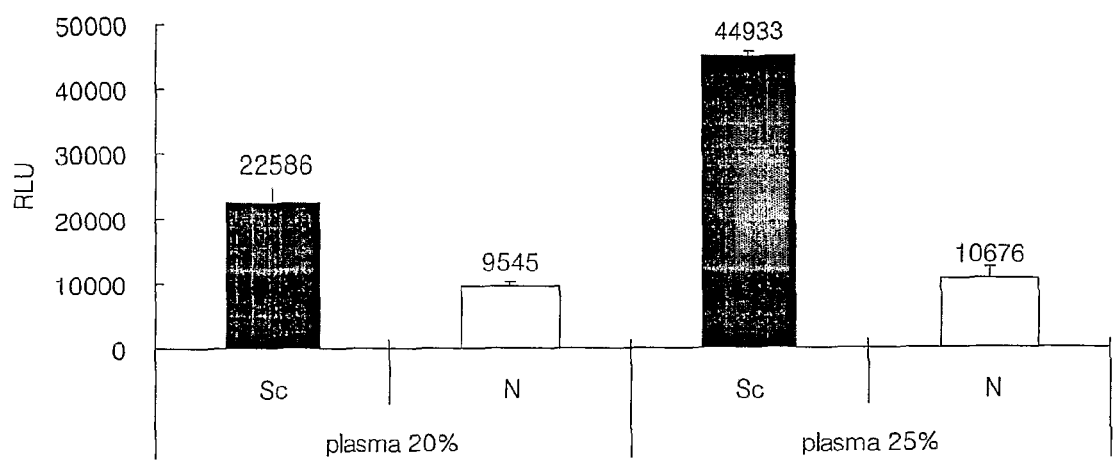
FIG. 12 represents the analysis results for detecting multimeric prion proteins in plasma with concentrations of 20% and 25% according to the MDS-3D-Single Bead System.

In addition, the 3E7-bead antibody and the T2-HRP antibody were used at a ratio of 1 to 1 and plasma samples in concentrations of 20% and 25% were prepared using Tricine (pH 8.0) buffer. The volumes of the reactions containing 20% and 25% plasma samples were 300 µl and 400 µl, respectively. The other procedures are the same as Example II. As shown in FIG. 12, the 25% plasma concentration was observed to produce much higher signal intensities and differentiation than 20% plasma concentration.

Example VII

Detection of Multimeric PrP in Plasma Using MDS-3D-Dual Bead System

Figure 8:
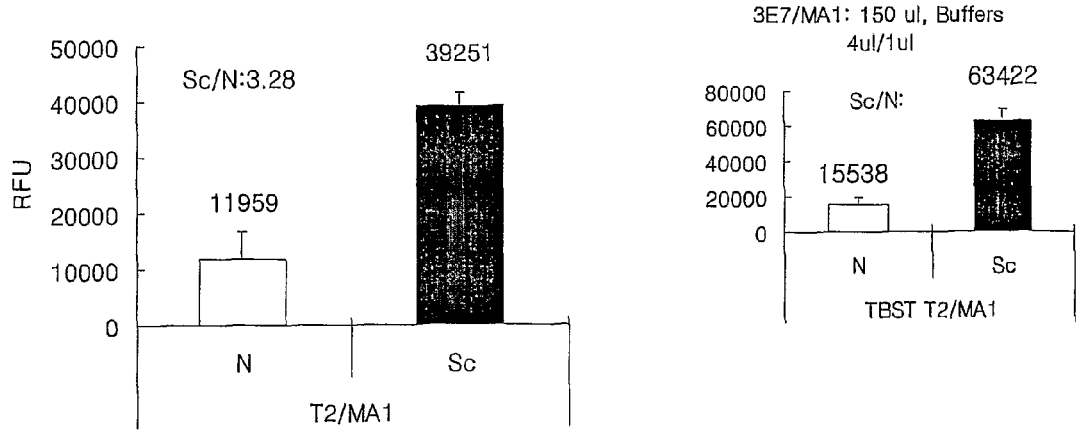
FIG. 8 shows the results of experiments for detecting multimeric prion proteins in plasma according to the MDS-3D-Dual Bead System using T2 and MAI 750 antibodies.

T2-conjugated magnetic bead as capturing antibodies and MAI 750-conjugated fluorescence latex bead as detection antibodies were used at a ratio of 2:1 or 4:1 for performing the MDS-3D-Dual Bead System. 15% plasma sample and TBST (pH 8.0) buffer were used. The other procedures are the same as Example III. As shown in FIG. 8, the Sc/N ratio and signal intensity are found to be higher at a 4:1 ratio of T2-bead to MAI 750-bead than a 2:1 ratio.

Example VIII

Figure 9:
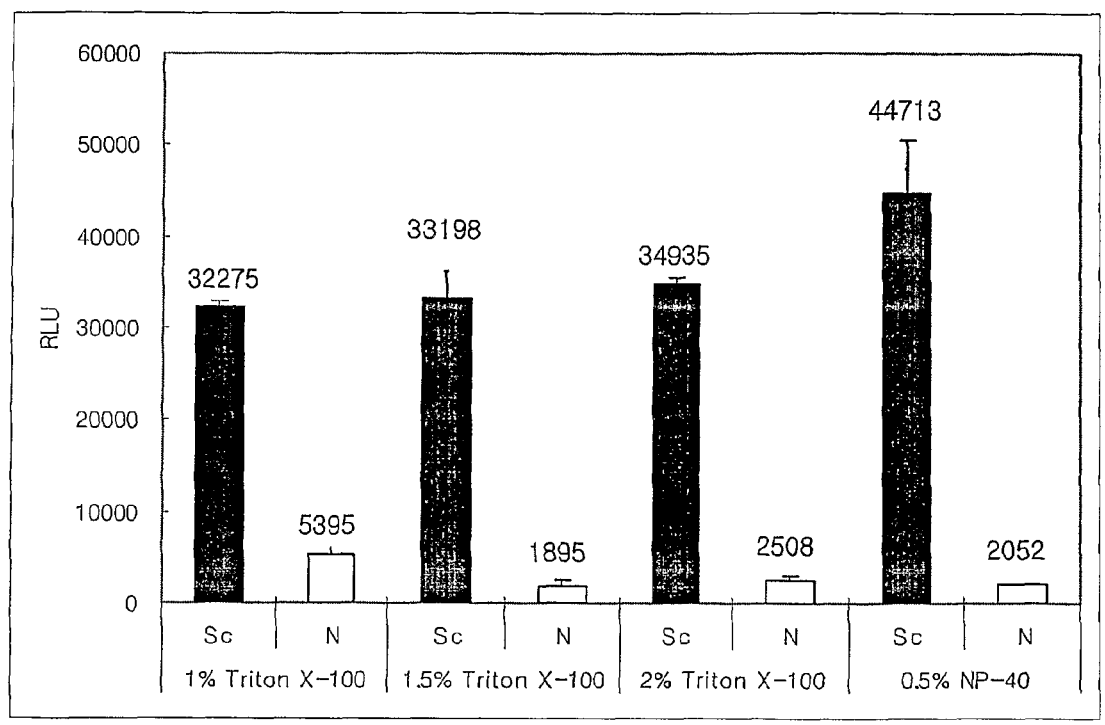
FIG. 9 shows the analysis results for detecting multimeric prion proteins in plasma according to the MDS-3D-Single Bead System with varying concentrations and types of detergent for preparing plasma samples.

Detection of Multimeric PrP in Plasma Using MDS-3D-Single Bead System with Varying Concentration and Type of Detergent The multimeric PrP in sheep plasma samples showing clinical signs to have PrP$^{sc}$ was detected in the MDS-3D-Single Bead System with varying concentrations and types of detergent in the same manner as Example II, except for detergent conditions. As shown in FIG. 9, concentrations of Triton X-IOO (1%, 1.5% and 2%) show similar detection and differentiation results to multimeric PrP. In addition, Np-40 (USB Corp., USA) also shows considerable detection and differentiation results, although the deviation of results is relatively high. Np-40 is one of nonionic detergents and represents [Octylphenoxy]polyethoxyethanol.

Example IX

Figure 10:
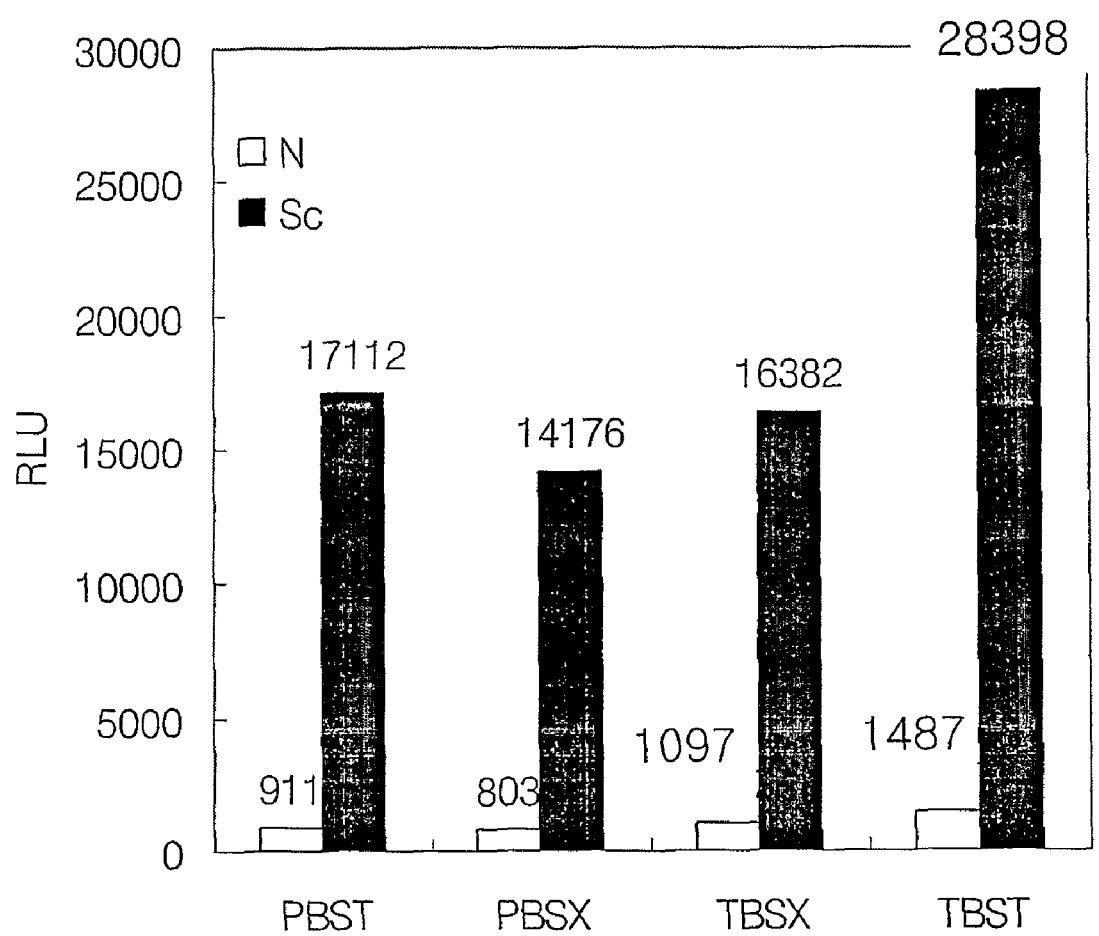
FIG. 10 represents the analysis results for detecting multimeric prion proteins in plasma according to the MDS-3D-Single Bead System with varying type of washing buffer for washing of beads incubated with plasma samples and antibodies.

Detection of Multimeric PrP in Plasma Using MDS-3D-Single Bead System with Varying Type of Washing Buffer The multimeric PrP in sheep plasma samples with PrP$^{sc}$ was detected in the MDS-3D-Single Bead System with varying the type of washing buffers used in washing of beads incubated with plasma samples and antibodies in the same manner as Example II, except for antibody weight ratio (3E7-bead:T2-HRP, 1:2) and washing conditions. As shown in FIG. 10, the TBST (tris-buffered saline with Tween 20) washing buffer exhibits most superior detection and differentiation results to multimeric PrP compared with other buffers, PBST (phosphate-buffered saline with Tween 20), PBSX (phosphate-buffered saline with Triton X-100) and TBSX (tris-buffered saline with Triton X-100).

Example X

Figure 13:
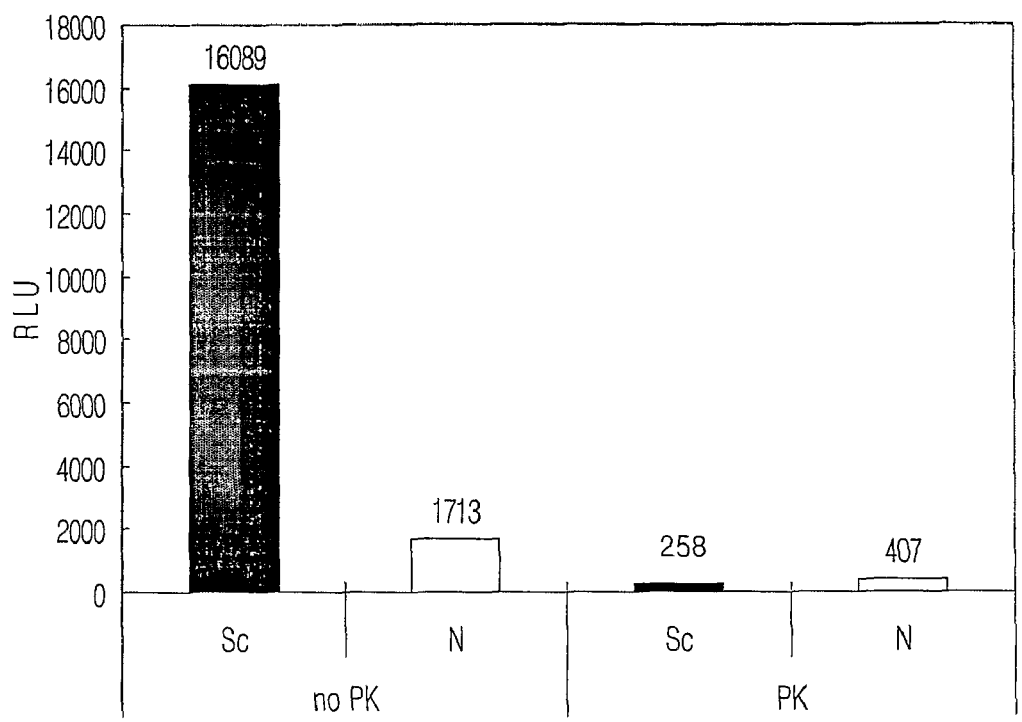
FIG. 13 shows influence of PK digestion on the detection of multimeric prion proteins in plasma according to the MDS-3D-Single Bead System.

Influence of PK Digestion on Detection of Multimeric PrP in Plasma Using MDS-3D-Single Bead System The multimeric PrP in sheep plasma samples with PrP$^{sc}$ was detected in the MDS-3D-Single Bead System with or without PK (protease K) digestion in the same manner as Example II, except that antibody weight ratio (3E7-bead:T2-HRP, 1:4). As shown in FIG. 13, the PK digestion greatly decreases signal intensities to PrP$^{Sc}$ in plasma samples. In this connection, it could be recognized that the MDS-3D-Single Bead System of this invention permits to completely eliminate a need of PK digestion in the detection of PrP$^{Sc}$ in blood or plasma samples.

Example XI

Figure 14A:
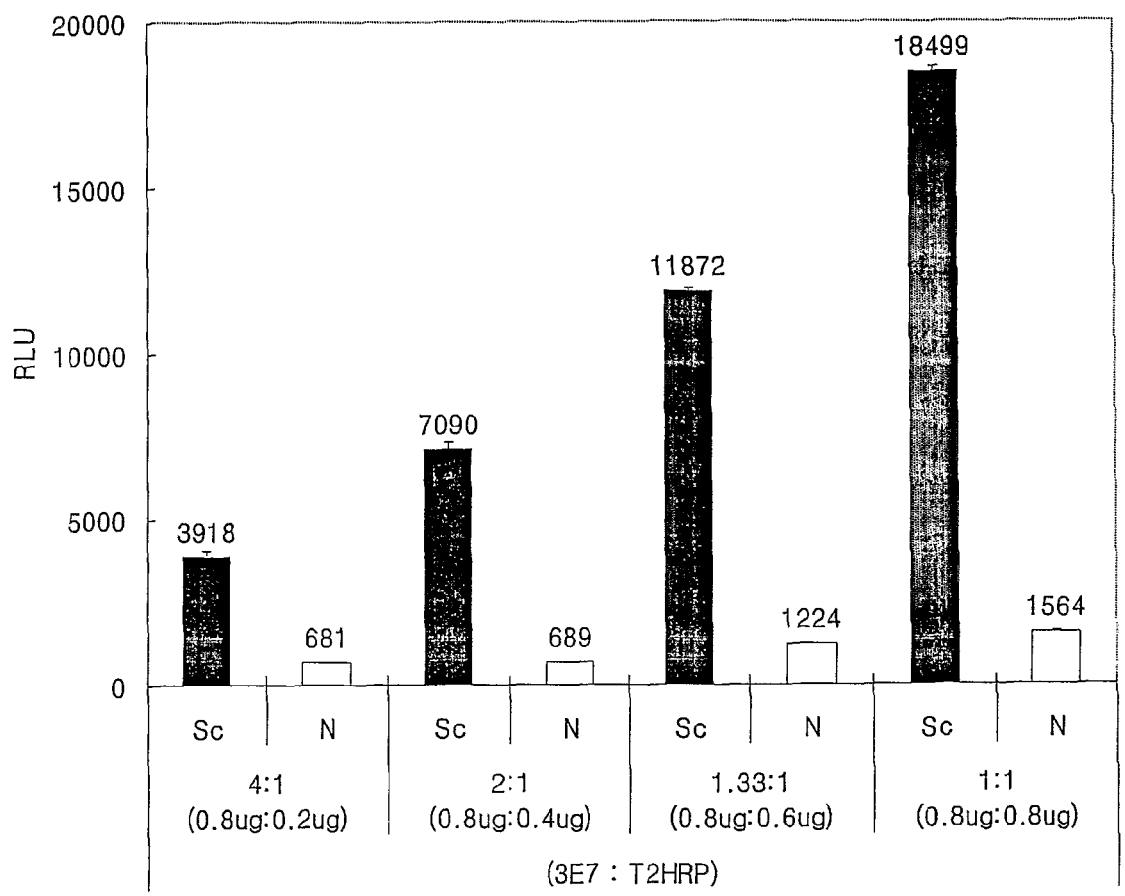
FIG. 14a represents the analysis results for detecting multimeric prion proteins in plasma according to the MDS-3D-Single Bead System with varying weight ratios of antibodies.

Detection of Multimeric PrP in Plasma Using MDS-3D-Single Bead System with Varying Weight Ratios of Antibodies The multimeric PrP in sheep plasma samples with PrP$_{sc}$ was detected in the MDS-3D-Single Bead System with varying weight ratios of antibodies in the same manner as Example II. The weight ratios of 3E7-bead capturing antibody to T2-HRP detection antibody were 4:1, 2:1, 1.33:1 and 1:1. As shown in FIG. 14a, where two antibodies were utilized in the same amount, the MDS-3D-Single Bead System of this invention exhibits most excellent detection and differentiation potentials to PrP$^{sc}$ in plasma samples.

Example XII

Figure 14B:
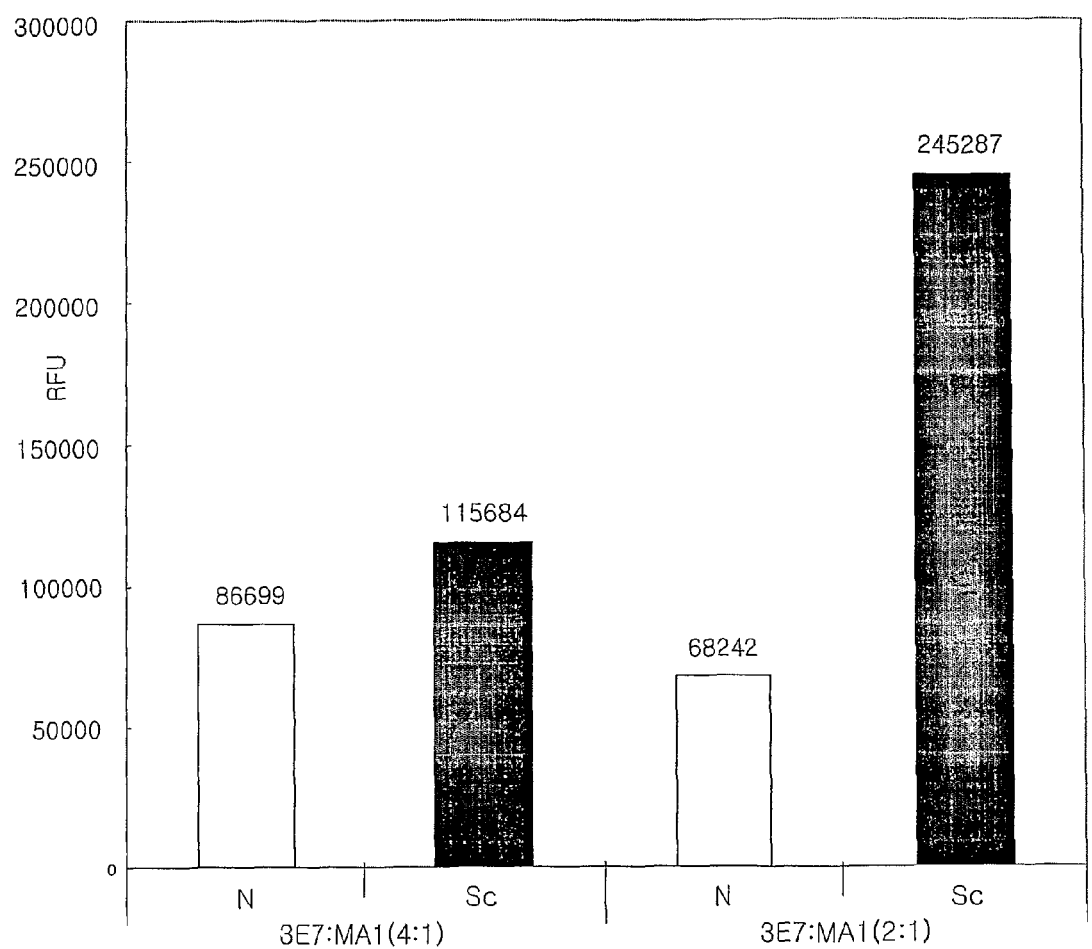
FIG. 14b represents the analysis results for detecting multimeric prion proteins in plasma according to the MDS-3D-Dual Bead System with varying weight ratios of antibodies.

Detection of Multimeric PrP in Plasma Using MDS-3D-Dual Bead System with Varying Weight Ratios of Antibodies The multimeric PrP in sheep plasma samples with PrP$_{sc}$ was detected in the MDS-3D-Dual Bead System with varying weight ratios of antibodies in the same manner as Example III. The weight ratios of 3E7-bead capturing antibody to MAI 750 fluorescence bead detection antibody were 4:1 and 2:1. As shown in FIG. 14b, where the capturing and detection antibodies were utilized at a ratio of 2:1, the MDS-3D-Dual Bead System of this invention exhibits most excellent detection and differentiation potentials to PrP$^{sc}$ in plasma samples.

Example XIII

Figure 15A:
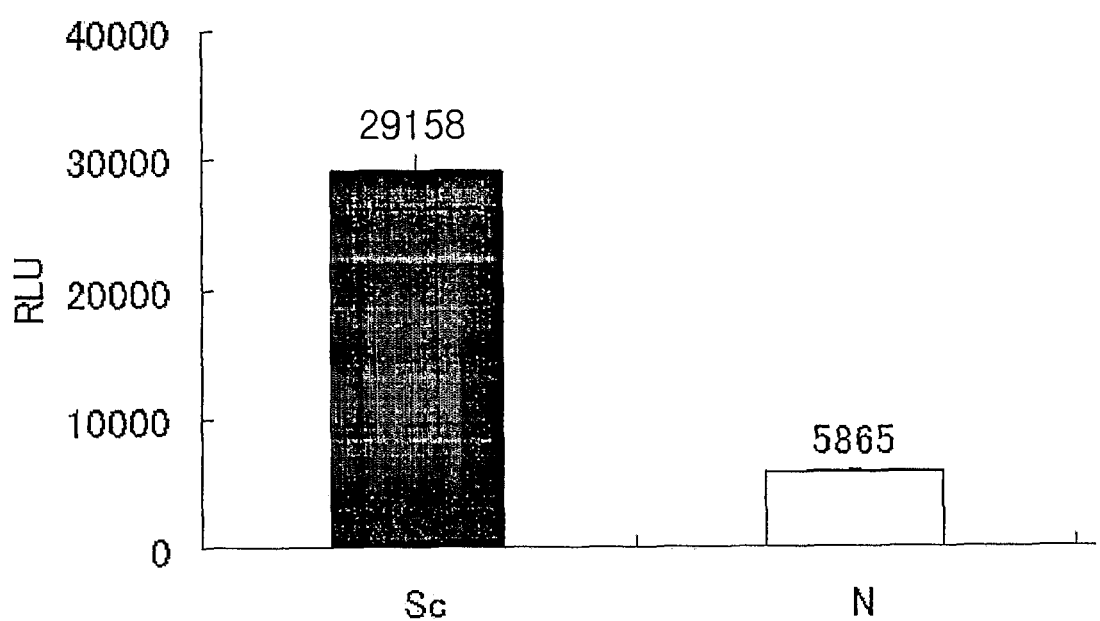
FIGS. 15a and 15b represent the analysis results for detecting multimeric prion proteins in plasma according to the MDS-3D-Single Bead System with capturing antibody cocktail.
Figure 15B:
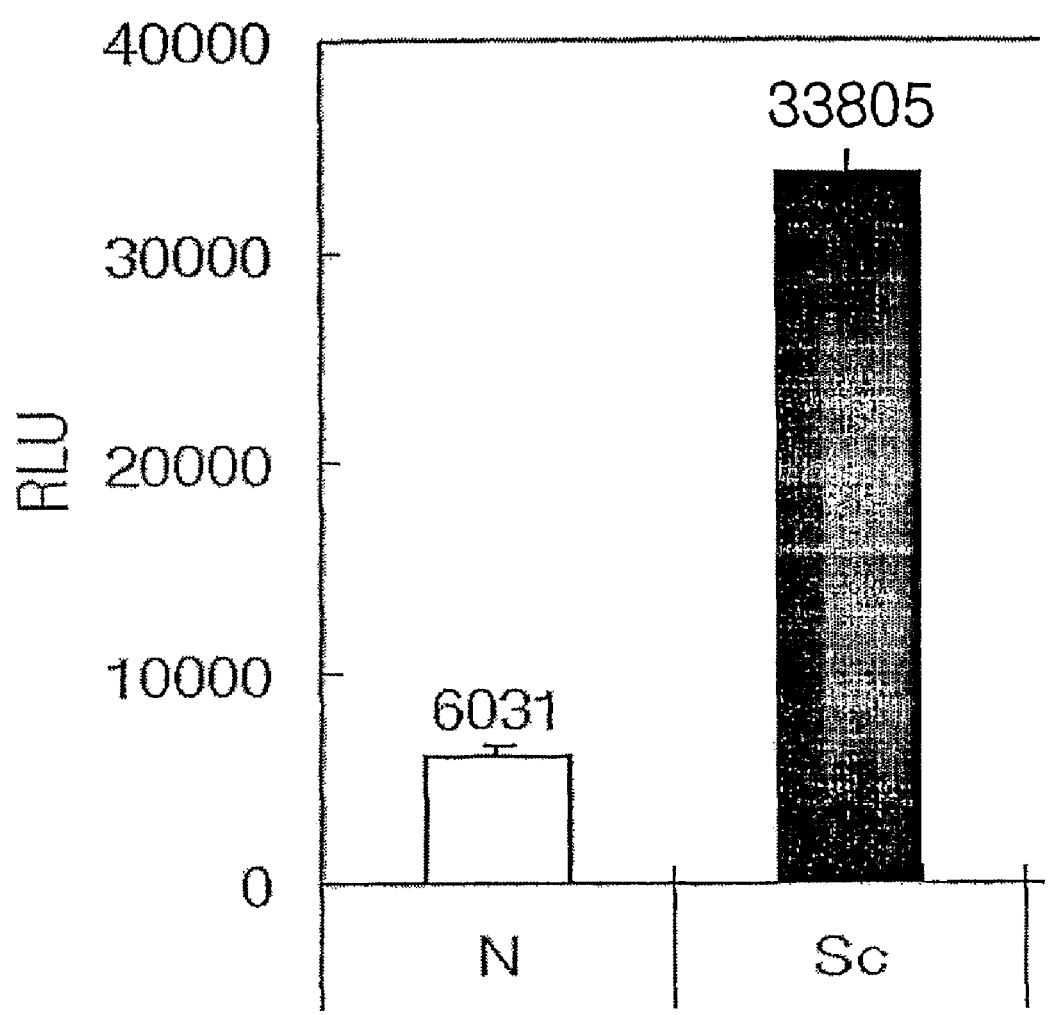

Detection of Multimeric PrP in Plasma Using MDS-3D-Single Bead System with Capturing Antibody Cocktail The multimeric PrP in sheep plasma samples with PrP$^{sc}$ was detected in the MDS-3D-Single Bead System with a capturing antibody cocktail in the same manner as Example IL. As a capturing antibody, the capturing antibody cocktail consisting of 3E7-bead and T2-bead antibodies (FIG. 15a) or 3E7-bead and MAI-bead antibodies (FIG. 15b) was used. The weight ratio of the capturing antibody cocktail to the detection antibody, T2-HRP was 1:1. As shown in FIGS. 15a and 15b, the capturing antibody cocktail also shows excellent detection and differentiation potentials to PrP$^{sc}$ in plasma samples.

Example XIV

Figure 15C:
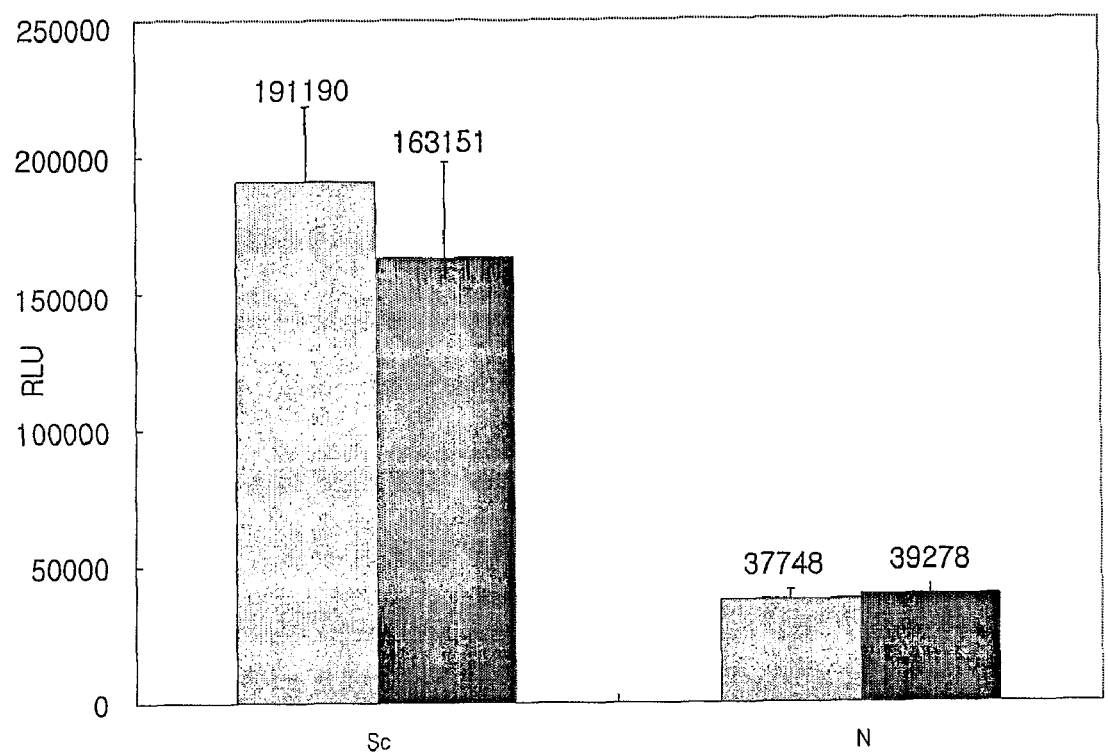
FIG. 15c represents the analysis results for detecting multimeric prion proteins in plasma according to the MDS-3D-Single Bead System with detection antibody cocktail. Left and right bars correspond to (i) 3E7-bead as a capturing antibody and T2-biotin and MAI-biotin as a detection antibody cocktail and (ii) MAI-bead as a capturing antibody and T2-biotin and 3E7-biotin as a detection antibody cocktail, respectively.

Detection of Multimeric PrP in Plasma Using MDS-3D-Single Bead System with Detection Antibody Cocktail The multimeric PrP in sheep plasma samples with PrP$^{sc}$ was detected in the MDS-3D-Single Bead System with a detection antibody cocktail in the same manner as Example II. The antibody sets used were (i) 3E7-bead as a capturing antibody and T2-biotin and MAI-biotin as a detection antibody cocktail and (ii) MAI-bead as a capturing antibody and T2-biotin and 3E7-biotin as a detection antibody cocktail. As shown in FIG. 15c, the detection antibody cocktails also show excellent detection and differentiation potentials to PrP$^{sc}$ in plasma samples.

Example XV

Comparison of Detection Potentials of MDS and MDS-3D-Single Bead System under Same Conditions The present inventors had already proposed a prototype process for differentially detecting a multimeric form from a monomeric form of a multimer-forming polypeptide, called "Multimer Detection System (MDS)" and filed for patent application under PCT (PCT/KR2005/004001).

For comparing PrP$^{Sc}$ detection and differentiation potentials of MDS and MDS-3D Single Bead System in a reliable manner, the multimeric PrP in sheep plasma samples with PrP$^{sc}$ was detected according each procedure under same experimental conditions. 3E7 and T7 antibodies were used as capturing and detection antibodies, respectively.

Figure 16:
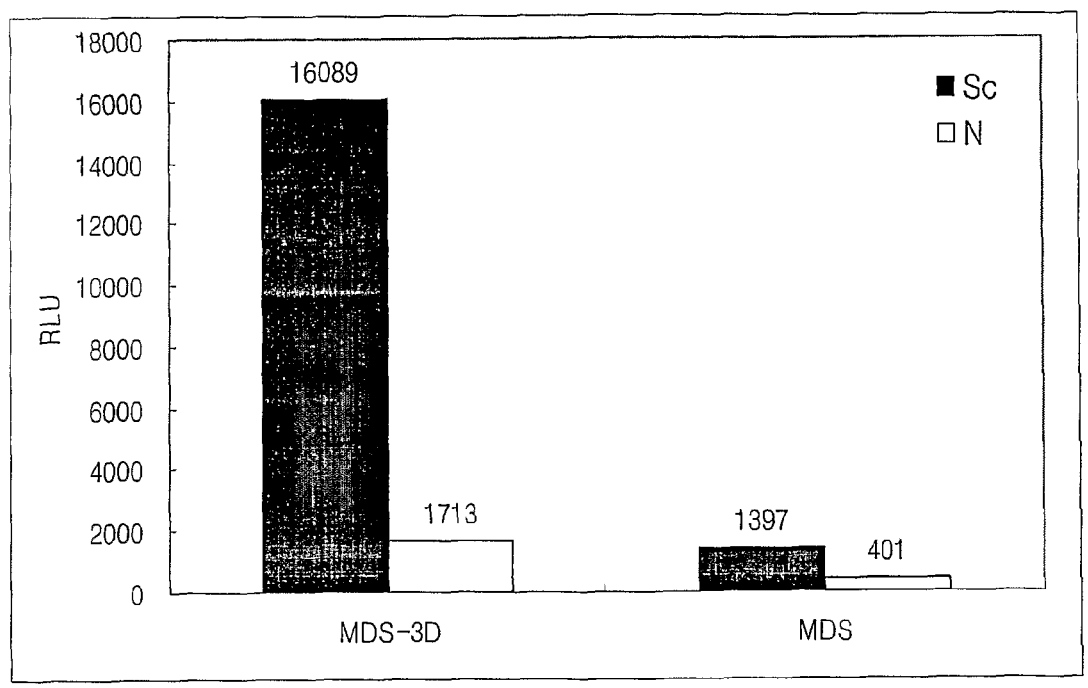
FIG. 16 demonstrates the comparison of detection potentials of MDS and MDS-3D Single Bead System.

As represented in FIG. 16, it becomes evident that the MDS-3D Single Bead System of this invention shows much higher sensitivity and differentiation potentials to PrP$^{sc}$ in sheep plasma samples than the MDS.

Example XVI

Determination of Plasma Concentration Suitable in MDS-3D-Single Bead System with Other Antibody Set The multimeric PrP in sheep plasma samples with PrP$^{sc}$ was detected in the MDS-3D-Single Bead System in the same manner as Example II, except for the type of antibody set and plasma concentration. ICSM35-biotin streptavidin bead as a capturing antibody and 1E4-HRP as a detection antibody were utilized. The concentration of sheep plasma was 25%. The ICSM35 antibody (D-Gen, Inc.) recognizes the epitope corresponding to the amino acid sequence spanning 96-105 (with reference to a sheep prion sequence) or 104-113 (with reference to a bovine prion sequence). The 1E4 antibody (Sanquin Reagents, Inc.) recognizes the epitope corresponding to the amino acid sequence spanning 100-111 (with reference to a sheep prion sequence) or 108-119 (with reference to a bovine prion sequence).

Figure 17:
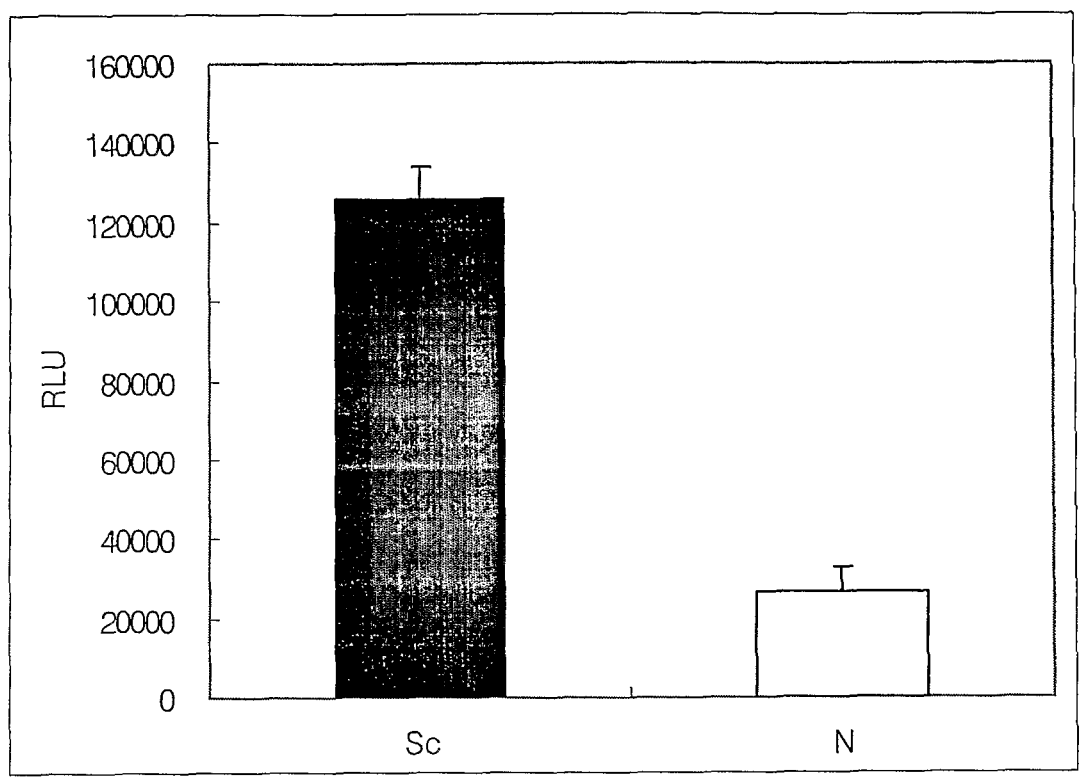
FIG. 17 represents the analysis results for detecting multimeric prion proteins $PrP^{Sc}$ in plasma samples by using an antibody set (ICSM35/1E4) recognizing partial overlapping epitopes.

As shown in FIG. 17, another antibody set recognizing partial overlapping epitopes also exhibits excellent sensitivity and differentiation potentials to PrP$^{sc}$ in plasma samples.

Having described a preferred embodiment of the present invention, it is to be understood that variants and modifications thereof falling within the spirit of the invention may become apparent to those skilled in this art, and the scope of this invention is to be determined by appended claims and their equivalents.

What is claimed is:

1. A method for differentially detecting a multimeric form from a monomeric form of a multimer-forming polypeptide in a biosample, comprising:
    (a) preparing a carrier-capturing antibody conjugate by binding a capturing antibody to the surface of a solid phase carrier in a three dimensional manner, wherein the capturing antibody is capable of recognizing an epitope on the multimer-forming polypeptide, and the solid phase carrier has a three dimensional structure;
    (b) preparing a detection antibody, wherein the epitope recognized by the capturing antibody has an amino acid sequence which overlaps, but is not identical to, with that of the epitope recognized by the detection antibody so that the capturing antibody and detection antibody when bound to their epitopes induce steric hindrance or are competitive in binding; wherein the epitope recognized by the capturing antibody and the epitope recognized by the detection antibody are not repeated in the multimer-forming polypeptide, and wherein the detection antibody has a label generating a detectable signal;
    (c) contacting simultaneously the carrier-capturing antibody conjugate and the detection antibody to the biosample;
    (d) separating carrier-capturing antibody-multimeric form-detection antibody complexes and carrier-capturing antibody-monomeric form complexes, from detection antibody-monomeric form complexes by washing out detection antibody-monomeric form complexes; and
    (e) detecting the formation of a carrier-capturing antibody-multimeric form-detection antibody complex by measuring a signal generated from the label linked to the detection antibody.

2. The method according to claim 1, wherein the detection antibody is bound to the surface of a solid phase carrier in a three dimensional manner, wherein the solid phase carrier has a three dimensional structure.

3. The method according to claim 1, wherein the multimer-forming polypeptide is selected from the group consisting of Aβ peptide, β-amyloid, tau protein, prion, α-synuclein, Ig light chains, serum amyloid A, transthyretin, cystatin C, $β_2$-microglobulin, huntingtin, superoxide dismutase, serpin and amylin.

4. The method according to claim 3, wherein the multimer-forming polypeptide is prion.

5. The method according to claim 4, wherein the monomeric form is $PrP^c$ and the multimeric form is $PrP^{Sc}$.

6. The method according to claim 1, wherein the solid phase carrier bound to the capturing antibody is a magnetic bead.

7. The method according to claim 2, wherein the solid phase carrier bound to the detection antibody is a latex bead.

8. The method according to claim 2, wherein the solid phase carrier bound to the detection antibody has a label generating a detectable signal.

9. The method according to claim 8, wherein the step (e) is carried out by measuring a signal generated from the label linked to the solid phase carrier bound to the detection antibody.

10. The method according to claim 1, wherein the label linked to the detection antibody is a chemical, an enzymatic, a radioactive, a fluorescent, a luminescent, a chemiluminescent or a FRET label.

11. The method according to claim 1, wherein the biosample is a brain homogenate or blood.

12. The method according to claim 11, wherein the biosample is blood.

13. The method according to claim 12, wherein the biosample is plasma.

14. The method according to claim 11, wherein the method further comprises pretreating the biosample with protease K or trypsin when the brain homogenate is used as the biosample.

15. The method according to claim 1, wherein the capturing antibody bound to the carrier and the detection antibody in the step (c) are used at 2:1-1:2 mole ratio of the capturing antibody to the detection antibody.

16. A kit for differentially detecting a multimeric form from a monomeric form of a multimer-forming polypeptide in a biosample, which comprises:
    (a) a capturing antibody recognizing an epitope on the multimer-forming polypeptide and bound three-dimensionally to the surface of a solid phase carrier having a three dimensional structure; and
    (b) a detection antibody; wherein the epitope recognized by the capturing antibody has the amino acid sequence which overlaps with, but is not identical to, that of the epitope recognized by the detection antibody so that the capturing antibody and detection antibody when bound to their epitopes induce steric hindrance or are competitive in binding; wherein the epitope recognized by the capturing antibody and the epitope recognized by the detection antibody are not repeated in the multimer-forming polypeptide, wherein the detection antibody has a label generating a detectable signal.

17. The kit according to claim 16, wherein the detection antibody is bound to the surface of a solid phase carrier in a three dimensional manner, wherein the solid phase carrier has a three dimensional structure.

18. The kit according to claim 16, wherein the multimer-forming polypeptide is selected from the group consisting of Aβ peptide, β-amyloid, tau protein, prion, α-synuclein, Ig light chains, serum amyloid A, transthyretin, cystatin C, $β_2$-microglobulin, huntingtin, superoxide dismutase, serpin and amylin.

19. The kit according to claim 18, wherein the multimer-forming polypeptide is prion.

20. The kit according to claim 19, wherein the monomeric form is $PrP^c$ and the multimeric form is $PrP^{Sc}$.

21. The method according to claim 8, wherein the label linked to the detecting antibody is one selected from the group consisting of a chemical, an enzymatic, a radioactive, a fluorescent, a luminescent, a chemiluminescent and a FRET label.

22. The kit according to claim 17, wherein the solid phase carrier bound to the detection antibody has a label generating a detectable signal.

* * * * *